(12) United States Patent
Ghodrati et al.

(10) Patent No.: US 12,394,522 B2
(45) Date of Patent: Aug. 19, 2025

(54) SYSTEM, APPARATUS, AND METHODS FOR HEALTH MONITORING

(71) Applicant: IntelliCare Technologies LLC, Hopkinton, MA (US)

(72) Inventors: Alireza Ghodrati, Hopkinton, MA (US); Alireza Mahmoudieh, Merced, CA (US)

(73) Assignee: INTELLICARE TECHNOLOGIES LLC, Hopkinton, MA (US)

( * ) Notice: Subject to any disclaimer, the term of this patent is extended or adjusted under 35 U.S.C. 154(b) by 470 days.

(21) Appl. No.: 17/697,563

(22) Filed: Mar. 17, 2022

(65) Prior Publication Data
US 2022/0351852 A1 Nov. 3, 2022

Related U.S. Application Data

(63) Continuation-in-part of application No. 16/874,303, filed on May 14, 2020, now abandoned.
(Continued)

(51) Int. Cl.
*G16H 40/67* (2018.01)
*A61B 5/00* (2006.01)
(Continued)

(52) U.S. Cl.
CPC .......... *G16H 40/67* (2018.01); *A61B 5/0002* (2013.01); *A61B 5/7275* (2013.01); *A61B 5/746* (2013.01);
(Continued)

(58) Field of Classification Search
CPC ..... A61B 5/0002; A61B 5/7275; A61B 5/746; A61B 5/7221
See application file for complete search history.

(56) References Cited

U.S. PATENT DOCUMENTS

2004/0015058 A1* 1/2004 Besson ............... H03F 3/45103
600/27
2006/0293570 A1 12/2006 Croghan et al.
(Continued)

FOREIGN PATENT DOCUMENTS

WO 2016110804 A1 7/2016

OTHER PUBLICATIONS

International Search Report and Written Opinion, PCT/US2022/020967, dated Jun. 17, 2022, 13 pages.

*Primary Examiner* — Catherine M Voorhees
*Assistant Examiner* — James Moss
(74) *Attorney, Agent, or Firm* — Potomac Law Group, PLLC; Reza Sadr; Reza Mollaaghababa

(57) ABSTRACT

A health monitoring system comprises at least one sensor configured to measure at least one parameter relating to a condition of a subject; and a health monitoring module in communication with the at least one sensor and configured to receive from the at least one sensor a measurement of the at least one parameter; based on the measurement, generate a message; and send the message to a health operator related to the subject. Moreover, in some embodiments, the health monitoring module is further configured to determine a confidence factor for the measurement. Further, in some embodiments the health monitoring module is also configured to receive from the at least one sensor a plurality of measurements of the at least one parameter; derive a trend for the plurality of measurements; and based on the trend, determine a health state for the subject.

12 Claims, 24 Drawing Sheets

Related U.S. Application Data

(60) Provisional application No. 63/255,798, filed on Oct. 14, 2021, provisional application No. 63/162,888, filed on Mar. 18, 2021, provisional application No. 62/847,573, filed on May 14, 2019.

(51) Int. Cl.
*G16H 20/10* (2018.01)
*G16H 40/20* (2018.01)
*G16H 50/30* (2018.01)

(52) U.S. Cl.
CPC ............ *G16H 20/10* (2018.01); *G16H 40/20* (2018.01); *G16H 50/30* (2018.01)

(56) References Cited

U.S. PATENT DOCUMENTS

| | | |
|---|---|---|
| 2011/0082711 A1 | 4/2011 | Poeze et al. |
| 2011/0112418 A1* | 5/2011 | Feild .................... A61B 5/0006 |
| | | 600/509 |
| 2011/0202495 A1* | 8/2011 | Gawlick ................ A61B 5/412 |
| | | 600/301 |
| 2012/0006100 A1* | 1/2012 | Gottlieb .............. A61M 5/1723 |
| | | 73/53.01 |
| 2012/0289788 A1* | 11/2012 | Jain ........................ A61B 5/165 |
| | | 702/19 |
| 2013/0158367 A1 | 6/2013 | Pacione et al. |
| 2014/0316220 A1 | 10/2014 | Sheldon |
| 2015/0265217 A1* | 9/2015 | Penders .................... A61B 5/33 |
| | | 600/300 |
| 2015/0289823 A1* | 10/2015 | Rack-Gomer ......... A61B 5/746 |
| | | 600/365 |
| 2015/0351690 A1* | 12/2015 | Toth .................... A61B 5/14542 |
| | | 600/391 |
| 2016/0278706 A1 | 9/2016 | Okamoto et al. |
| 2017/0100071 A1 | 4/2017 | Heikenfeld |
| 2017/0220938 A1 | 8/2017 | Sainani et al. |
| 2017/0265765 A1 | 9/2017 | Baumann et al. |
| 2017/0372026 A1 | 12/2017 | Sanyal et al. |
| 2018/0042493 A1* | 2/2018 | Muehlsteff ........... A61B 5/7275 |
| 2018/0310822 A1* | 11/2018 | Indorf .................. A61B 5/7275 |
| 2019/0110751 A1 | 4/2019 | Lee et al. |
| 2019/0246973 A1* | 8/2019 | Constantin ............. G16H 40/67 |
| 2020/0155018 A1* | 5/2020 | Igami ................ A61B 5/02444 |
| 2020/0196865 A1 | 6/2020 | Kamath et al. |
| 2020/0205704 A1* | 7/2020 | Vanslyke ............... G16H 20/60 |

\* cited by examiner

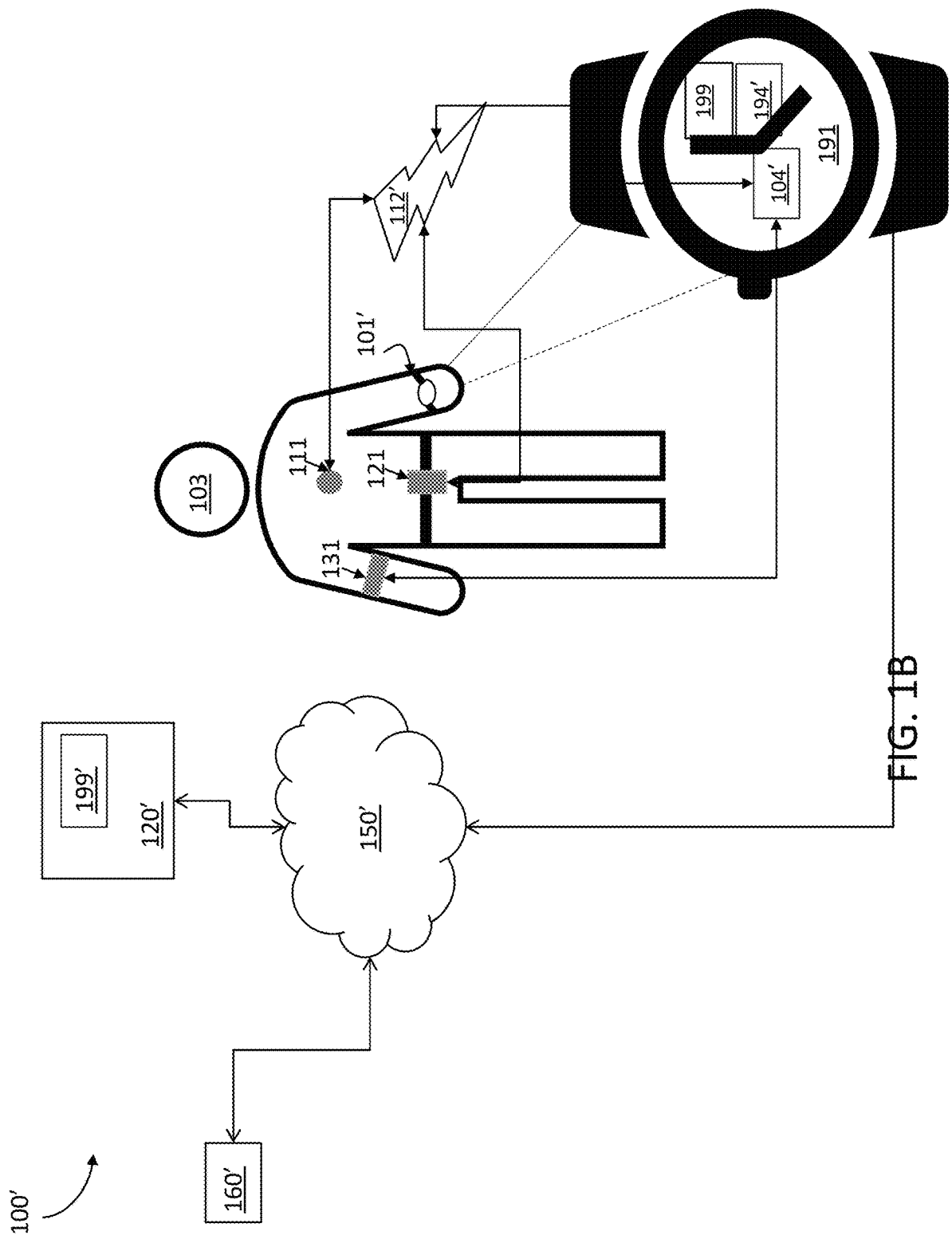

SYSTEM, APPARATUS, AND METHODS FOR HEALTH MONITORING

RELATED APPLICATIONS

This utility Application claims the benefit of priority in U.S. provisional Application No. 63/162,888, filed Mar. 18, 2021; and U.S. provisional Application No. 63/255,798, filed Oct. 14, 2021, both of which are entitled "SYSTEM, APPARATUS, AND METHODS FOR HEALTH MONITORING". Further, this utility Application is a continuation in part of U.S. Utility application Ser. No. 16/874,303, filed on May 14, 2020, itself claiming the benefit of priority in the U.S. provisional Application No. 62/847,573, filed on May 14, 2019, and both entitled "SYSTEM, APPARATUS, AND METHODS FOR REMOTE HEALTH MONITORING". The entire contents of the above applications are incorporated herein by reference.

TECHNICAL FIELD

The present disclosure generally relates to health monitoring, and more particularly to methods, apparatus, devices, and systems for monitoring health of a subject locally or remotely.

BACKGROUND

Most seniors suffer from one or more chronic conditions such as hypertension and diabetes, which need continuous management. At the same time, many elderly and senior citizen individuals often wish to live independently at their own home. Children, loved ones, and relatives of such individuals may also wish to respect these individuals' wishes for living independently, although worrying about their health and wishing that they could be kept informed of their health status and be alerted if/when help is needed. While existing assistive remote care technologies can provide peace of mind by monitoring these individuals, these technologies are often intrusive (e.g., use of video cameras) or require a person's active participation in the monitoring (e.g., pressing a button when a fall occurs).

Existing remote health monitoring technologies suffer from some major issues that reduce their effectiveness. For example, some of these technologies use physiological data that are collected at home, data that can be erroneous and unreliable. Further, some technologies use platforms that mainly transfer data and apply simple threshold-based algorithms, with few actionable alerts for caregivers and physicians. Such mechanisms increase the risk of false alarms. Also, in these technologies, patient engagement levels are generally low, and human interaction elements that are added to encourage use of the technology may increase the burden of chronic care management.

SUMMARY

The present disclosure relates to remote health monitoring of subjects, such as the elderly, senior citizens, individuals having chronic health issues, or individuals requiring assistance in managing their health or physiological condition.

In some embodiments, the techniques described herein relate to a health monitoring system including at least one sensor configured to measure at least one parameter relating to a condition of a subject; and a health monitoring module in communication with the at least one sensor and configured to: receive from the at least one sensor a measurement of the at least one parameter; based on the measurement, generate a message; and send the message to a health operator related to the subject.

In some embodiments, the techniques described herein relate to a health monitoring system, wherein the health monitoring module is further configured to detect a reliability error in the measurement of the at least one parameter.

In some embodiments, the techniques described herein relate to a health monitoring system, wherein the health monitoring module is further configured to determine a confidence factor for the measurement.

In some embodiments, the techniques described herein relate to a health monitoring system, wherein the health monitoring module is further configured to: receive from the at least one sensor a plurality of measurements of the at least one parameter; derive a trend for the plurality of measurements; and based on the trend, determine a health state for the subject.

In some embodiments, the techniques described herein relate to a health monitoring system, wherein the health monitoring module is further configured to include in the message a reminder to perform a new measurement based on the health state.

In some embodiments, the techniques described herein relate to a health monitoring system, wherein the health monitoring module is further configured to include in the message instructions for modifying medication of the subject.

In some embodiments, the techniques described herein relate to a health monitoring system, wherein the health monitoring module is further configured to: receive from the at least one sensor a plurality of measurements of the at least one parameter; perform a comparison of the plurality of measurements with at least one threshold value; and based on the comparison, determine a health state for the subject.

In some embodiments, the techniques described herein relate to a health monitoring system, wherein the confidence factor includes a raw data quality confidence factor, a behavior confidence factor, a physiological confidence factor, or a total confidence factor.

In some embodiments, the techniques described herein relate to a health monitoring system, wherein the health monitoring module is further configured to: store a plurality of measurements along with a plurality of confidence factors corresponding to the plurality of measurements; and derive an average of the plurality of measurements, wherein the average is a weighted average in which each measurement of the plurality of measurements is weighted by the corresponding confidence factor.

In some embodiments, the techniques described herein relate to a health monitoring system, further including a machine learning module configured to: receive a plurality of features corresponding to the measurement; and based on the features, determining a health state of the subject.

In some embodiments, the techniques described herein relate to a health monitoring system, wherein the condition of the subject is a physiological condition.

In some embodiments, the techniques described herein relate to a health monitoring system, wherein the condition of the subject is a behavioral condition.

In some embodiments, the techniques described herein relate to a health monitoring system, wherein: the message includes a coaching message that is based on the condition of the subject; and the health operator is the subject.

In some embodiments, the techniques described herein relate to a health monitoring system, wherein the message includes an alert, and the health operator is a caregiver of the subject.

In some embodiments, the techniques described herein relate to a health monitoring system, wherein the message includes an alert, and the health operator is a physician of the subject.

In some embodiments, the techniques described herein relate to a health monitoring system, wherein the health monitoring module includes an automated data collection module configured to: control automated measurements by a first sensor of the at least one sensor; determine a factor of the automated measurements based on the condition of the subject; and send a measurement command to the first sensor for performing the automated measurements based on the factor.

In some embodiments, the techniques described herein relate to a health monitoring system, wherein the factor is a frequency of the automated measurements.

In some embodiments, the techniques described herein relate to a health monitoring system, wherein the factor is a type of the automated measurements.

In some embodiments, the techniques described herein relate to a health monitoring system, wherein the health monitoring module is further configured to: detect a critical event based on the measurement; include in the message a critical condition alert message; and send the message to a health actor.

In some embodiments, the techniques described herein relate to a health monitoring system, wherein the health actor is a caregiver or a physician.

In one aspect, a system for remote health monitoring is featured. The featured system comprises one or more sensors each configured to detect a first plurality of parameters relating to one or more physiological conditions of a subject, an interface configured to receive a second plurality of parameters relating to the physiological condition(s) of the subject, where the second plurality of parameters can be generated by other sensors, and at least one processor coupled to the one or more sensors and the interface. The processor can be configured to monitor the first and second pluralities of parameters and, in an event at least one parameter falls outside of a predetermined range, issue an alarm signal indicating onset of an undesired event in the physiological condition(s) of the subject.

In another aspect, a system for health monitoring comprises one or more interfaces each configured to detect a plurality of parameters relating to physiological condition(s) of a subject and at least one processor coupled to the one or more interfaces. The processor can be configured to monitor the plurality of parameters and, in an event at least one parameter falls outside of a predetermined range, issue an alarm signal indicating onset of an undesired event in the physiological condition(s) of the subject.

In other examples, the aspects above, or any system, method, apparatus described herein can include one or more of the following features.

The at least one interface can comprise a sensor configured to detect at least one parameter relating to the physiological condition(s) of a subject. By way of example, the sensor(s) can comprise at least one of a heart rate detection sensor, a location determination sensor, a movement sensor, and a sensor connected to one or more medicine containers consumed by the subject. Further, the parameters can include information relating to at least one of medication intake by the subject, sleeping patterns of the subject, physical activity rate of the subject, blood pressure of the subject, weight of the subject, blood glucose level of the subject, physical state of the subject, and emotional state of the subject.

The predetermined range can comprise an expected range of values for the first and the second plurality of parameters. The processor can be configured to determine the expected range based on historical measures of the at least one parameter. For example, the processor can be configured to obtain the historical measures of the at least one parameter by storing measurement of the at least one parameter at two or more instants of time. Additionally or alternatively, the processor can be configured to determine a subject-specific expected range for the subject based on the historical measures. Further, the processor can be configured to monitor the parameters and, in an event the pluralities of parameters fall within the predetermined range, issue an all clear signal indicating that the subject is in a stable physiological condition. In some embodiments, the processor can be configured to monitor the at least one parameter over a predetermined time interval.

In some embodiments, the processor can be configured to issue the alarm signal to an entity capable of providing immediate assistance to the subject. Alternatively or additionally, the alarm signal can be a reminder signal issued to the subject.

In some embodiments, the health monitoring module is further configured to trigger a new automatic measurement or change the frequency of an automatic measurement based on the health state.

Other aspects and advantages of the embodiments can become apparent from the following drawings and description, all of which illustrate the various aspects of the embodiments, by way of example only.

BRIEF DESCRIPTION OF THE DRAWINGS

The drawings are not necessarily to scale or exhaustive. Instead, emphasis is generally placed upon illustrating the principles of the embodiments described herein. The accompanying drawings, which are incorporated in this specification and constitute a part of it, illustrate several embodiments consistent with the disclosure. Together with the description, the drawings serve to explain the principles of the disclosure.

In the drawings:

FIG. 1B depicts another high-level diagram of a system for remote health monitoring according to some embodiments disclosed herein.

DETAILED DESCRIPTION

Figure 1A:
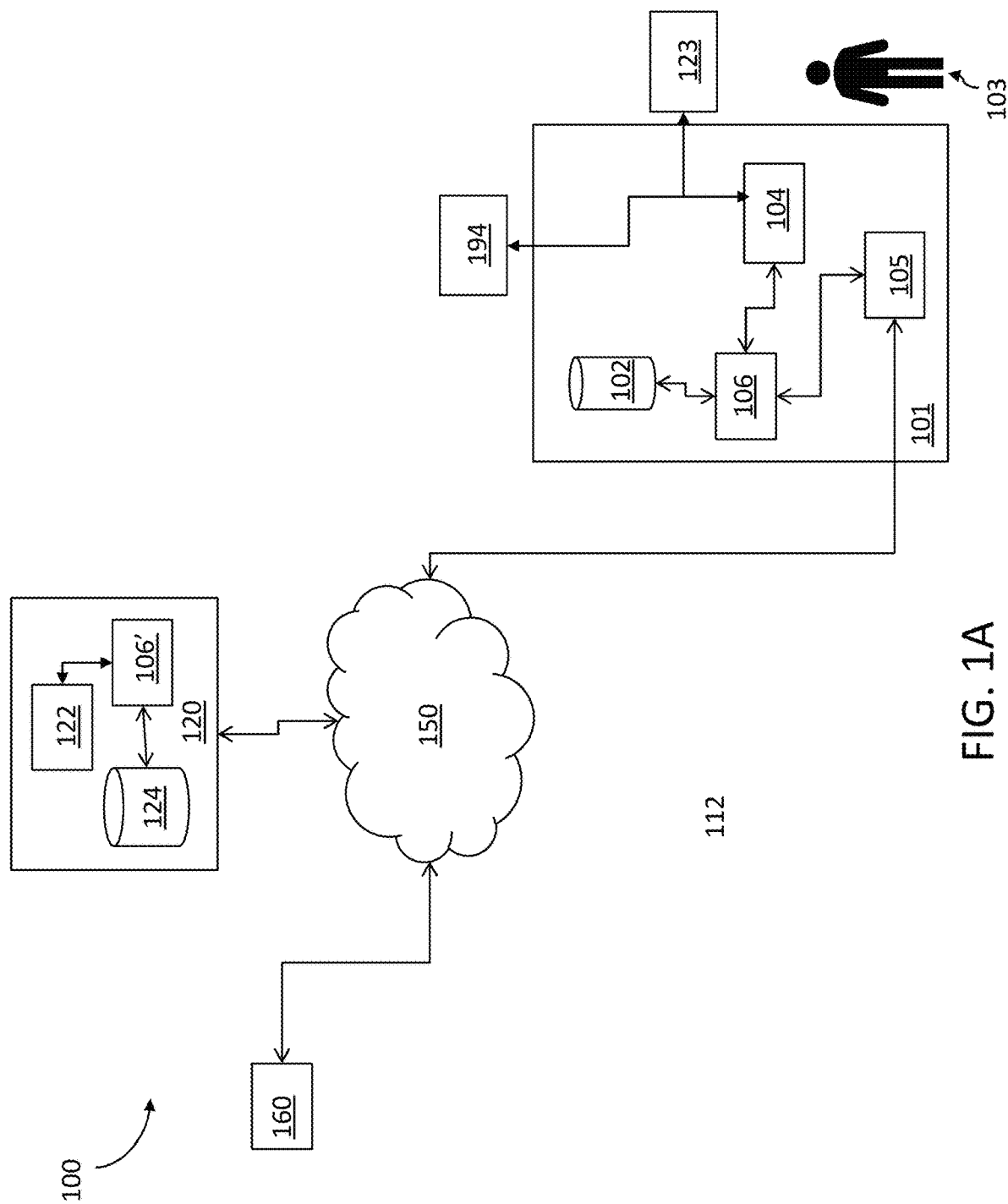
FIG. 1A depicts a high-level block diagram of a system for remote health monitoring according to some embodiments disclosed herein.

Various embodiments utilize health coaching and intervention modules and remote monitoring platforms and manage health issues such as hypertension, diabetes, heart failure, or atrial fibrillation based on monitoring of physiological and behavioral parameters. Some embodiments use artificial intelligence driven or behavioral based platforms that focus on key barriers to monitoring the health issue and intervention, based on proven clinical guidelines.

Some embodiments utilize mechanisms for automatically capturing one or more physiological and behavioral parameters using tools such as mobile applications (app) installed on a user's mobile device such as phone or wearable devices such as smart watches. The mobile applications may provide personalized coaching messages to the users. A remote monitoring platform may combine the automatic and personalized health coaching with advanced algorithms. The remote monitoring platform may alert the subject's designated care manager when appropriate. Some embodiments use a companion platform that is a web-based app and may provide remote access to subject data, evaluates the situation, and suggests interventions based on protocols developed by health professionals. Some embodiments utilize platforms that build personalized physiological and behavioral models for each subject based on the collected data and each person's risk factors. Such platforms may track overtime the health condition of the subject, such as her hypertension, diabetes, or heart failure.

Several embodiments provide multiple advantages over the existing technology. For example, some embodiments minimize measurement errors by determining the reliability of measurements or minimizing error sources to improve controlling the health issue and reducing false alarms. Moreover, some embodiments utilize a personalized plan of care by, for example, triggering measurement reminders adaptively according to the health state of a subject, or physiological and behavioral data collected from the subject. The data may be collected, for example, using mobile devices or wearables such as smart watches. Further, some embodiments provide behavioral coaching by initiating personalized lifestyle coaching in order to reduce healthcare staff workload and improve outcomes by increasing subject engagement. Further, some embodiments provide effective care coordination by tracking the health condition control state of the subject and triggering alerts only when further intervention is needed based on the personalized model.

Chronic diseases often affect the physical activity of a person. Among elderly, the progression of a chronic disease can be slow, and early symptoms of a chronic disease can go unnoticed. Further, since the senior citizen population often desires to live independently, among senior citizens and the elderly there is often a higher risk of delayed detection of symptoms and conditions that can lead to severe health problems. Therefore, there is a growing need for assistive care technologies, such as remote health monitoring systems that are configured to alert caregivers and other authorized parties with notifications regarding the health status of such individuals (e.g., the elderly and senior citizens). In addition to the elderly and senior citizen population, such systems can be used to monitor health status of other subjects, such as children or generally anyone having a chronic disease.

FIG. 1A-1B depict high-level block diagrams of a system 100 for remote health monitoring according to some embodiments disclosed herein. The system 100 can provide an unobtrusive remote care monitoring that covers different aspects of individual's health. Further, the system 100 can be configured to provide early notifications to caregivers of senior citizens and people with chronic diseases about deterioration and possible onset of conditions that require caregiver intervention or prevention of possible future complications.

The system 100 can comprise a health monitor 101 having at least one interface 104 configured to receive and collect information relating to a physiological condition of the subject 103. In some embodiments, the health monitor 101 can be implemented in a wearable device, such as a device configured for being worn around the wrist of the subject (e.g., implemented as a watch or in a watch). For example, the health monitor 101 can be implemented in hardware (in a chip) and included in a wearable device, such as a watch.

In some embodiments, the health monitor 101 can be implemented in an existing wearable device, such as a smart watch. Such wearables are suitable for long term and continuous monitoring of physiological and behavioral parameters along with the geographical information. They are easily available to public and many people already use these devices daily. Alternatively or additionally, the health monitor disclosed herein 101 can easily integrate with smart phones that most people carry with them. Smartphones can provide a great platform for patient awareness and collaborative caregiving by including family and caregivers in a care circle.

As detailed below, the health monitor 101 can be configured to collect physiological and behavioral parameters regarding the subject 103. The collected information can be stored locally (e.g., in a database 102) or transmitted via a communications network 150 to a server 120. The communications network 150 can be any suitable communications network known in the art. Also, the health monitor 101 can be configured to communicate with the communications network 150 and the server 120 via any suitable means known and available in the art (e.g., via a wireless or wired connection). By way of example, the health monitor 101 can comprise a communication interface 105 that allows establishing a Wi-Fi connection to connect to a communications network 150 (e.g., Internet) via local wireless networks. Additionally or alternatively, the interface 105 can comprise Bluetooth capabilities and be configured such that it can allow the health monitor 101 to communicate with other devices or portions of the systems (e.g., other wearables, sensors, etc.). Further, in some embodiments, the communications interface 105 can be configured to provide cellular communications or provide the health monitor 101 with a connection to the communications network 105 (e.g., the Internet) to carry data or voice.

The system 101 can further comprise an interface 104. The interface 104 can comprise one or more sensors, each configured to collect or obtain some information regarding at least some feature of the subject's physiological condition. The one or more sensors can comprise any sensors known in the art, for example, a positioning sensor (e.g., global positioning sensor (GPS)) for sensing the location of the subject, an accelerometer for detecting the subject's activities, a gyroscope for detecting the body posture of the subject 103, a heart rate detector, such as a red and infrared LED or a photodiode for heart rate measurement or reflective plethysmography to measure the blood oxygenation, an altimeter or a pressure sensor, or a temperature sensor. The one or more sensors can be locally disposed on the health monitor 101 or be positioned remote from the health monitor 101 and configured to communicate with the health monitor via a communications link.

For example, as shown in FIGS. 1A-1B, the health monitor 101 can be coupled to one or more sensors or interfaces 111, 121, 131 via one or more communications links 112, 122, 132. The communications links can be wireless or wired communications links. Further, as shown in FIG. 1B, the one or more additional sensors or interfaces 111, 121, 131 can be other sensors or wearables (e.g., a blood pressure monitor 121, a wearable ECG patch 131, or any other wearable sensor or interface 111) that are configured to transmit data to the health monitor 101. Additionally or alternatively, the one or more additional sensors or interfaces 111, 121, 131 can be physiological measurement systems that are configured to collect physiological parameters such as blood pressure, blood glucose, weight, respiratory flow, etc. These measurements can be done by the subject or with the help of the caregiver. The health monitor 101 can also connect to smart medication boxes or other medication management devices and collect information about person's medication adherence.

Generally, the information and parameters collected by the interface 104 can comprise any suitable information that can be useful in assessing and tracking the subject's physiological condition. For example, the one or more interfaces can collect information regarding at least one of the subject's heart rate, respiration rate, oxygen saturation, location, physical activity level, amount of sedentary behavior, posture and postural transition times, energy expenditure, occurrence of falls, gait and balance, tremor, and sleep patterns.

The information and data collected by the interface 104 can be forwarded to a processor 106 for processing, storage on a database 102, or for forwarding to a server 120. The processor 106 can be any suitable processor known in the art. The processor 106 can collect and process the physiological parameters collected by the interface 104 over time and detect possible outliers and inaccurate measurements due to improper measurement or motion artifacts.

In some embodiments, the processor 106 of the health monitor 101 can process the activity of the person along with physiological parameters to detect possible health issues. For example, after an activity such as climbing the stairs, the abnormal increase of the heart rate or abnormal decrease in the oxygen saturation can be interpreted by the processor 106 as a sign of a potential health issue, and tracked as an important event.

The processed and collected physiological and behavioral information along with important detected events can be transferred to a server 120 (e.g., a HIPAA compliant remote cloud server 120) in near real time through a secured internet connection. The information on the server 120 or loud server can be processed and depending on the caregiver preference and person's medical condition. Based on the processed information, alarms, notifications, and updates can be sent to caregiver phone or smart device 160 via secure internet connection. At any time, the caregiver can also acquire the latest information about the person's health status and latest physiological measurements. Various notifications can also be set on caregiver's smart device 160 based on the condition of the person that is monitored. For example for a patient with a cardiac disease, heart notifications can be set to notify caregiver about lower or higher heart rate than normal or irregular heart rhythm.

The server 120 can also be any suitable system known and available in the art having appropriate processing capabilities. For example, the server 120 can be a secure cloud server, such as a secure cloud server configured to store long term health data and provide insight to the data using advanced data analytics and algorithms.

The system 100 can facilitate and simplify capturing patient generated health data (PGHD) by providing a platform that optimize coordinated and collaborative caregiving by including family members and caregivers in a circle of care. Specifically, the system 100 can collect physiological and behavioral data with geographical information in real-time. In some embodiments, the data collected by the system 100 can be de-identified to remove any association with the subject(s) from whom the data have been collected. The de-identified data can be stored on a database 124 on the sever 120 and used by various entities, for example for determining possible outbreaks in communities by public health officials. The system 100 can also empower individuals and their caregivers to be aware of the individual's health status and proper intervention by the caregivers can prevent more severe illnesses.

In some embodiments, the data obtained by the health monitor 101 can comprise continuous and long-term physiological data that can be used to accurately and quickly diagnose patients who have been exposed to pathogens.

In some embodiment, the processor (server processor 122 or local processor 106) can calculate a health score in real time for each person based on the subject's age, weight, height, activity, mental status, and physiological parameters. By way of example, the health score can have a value ranging between 0 to 100, where having a higher value of health score can indicate that the subject is in a better health status than those having lower scores. The trend of this value over time can indicate deterioration of the subject's health (if the score decreases) or improvement of the subject's health status (if the score increases). This score can be used as a marker for the effectiveness of a treatment or side effects of a medication.

The information transmitted to the caregiver can also include the wearable's status in terms of the battery lifetime, connection to the communication network 150 (e.g., Internet) and whether they are worn by the subject, and if not worn, the last time it was worn.

The caregiver can set notifications on his/her device based on different parameters, such as the distance of the person from home, the amount of time the person has been outside home, sleep pattern and number of interrupts during sleep, low battery of the wearable, low activity and high sedentary time during the day.

On the remote server 120, short term and long term physiological and behavioral parameters of the person can be processed according to the person's own data and the data of other people with similar health conditions. Significant variation of the statistical properties of those parameters can be detected as possible health issues and the assigned caregiver can be notified about the potential health condition.

In some embodiments, the remote server 120 can also analyze a correlation, if any, between the medications taken by the person with the physiological parameters and inform the caregiver about the effectiveness of the medications. Further, the tele-monitoring system can be configured so that multiple caregivers or relatives can receive status updates about a single subject or one caregiver can receive status updates about multiple subjects.

In some embodiments, the system can also include a voice enabled assistant on the health monitor 101 or a separate system that communicates verbally with the subject. This verbal communication can include reminders for medications, messages that encourage more activity, or messages that verify that the subject has taken his/her medication(s). The voice enabled assistant can also be configured to communicate with the subject to ask questions about the mood, level of pain and other possible symptoms of the person, and collect this information for better health assessment. In some embodiments, the verbal communication can include puzzles or mind games that are configured to quantify the mental status of the subject.

Figure 1C:
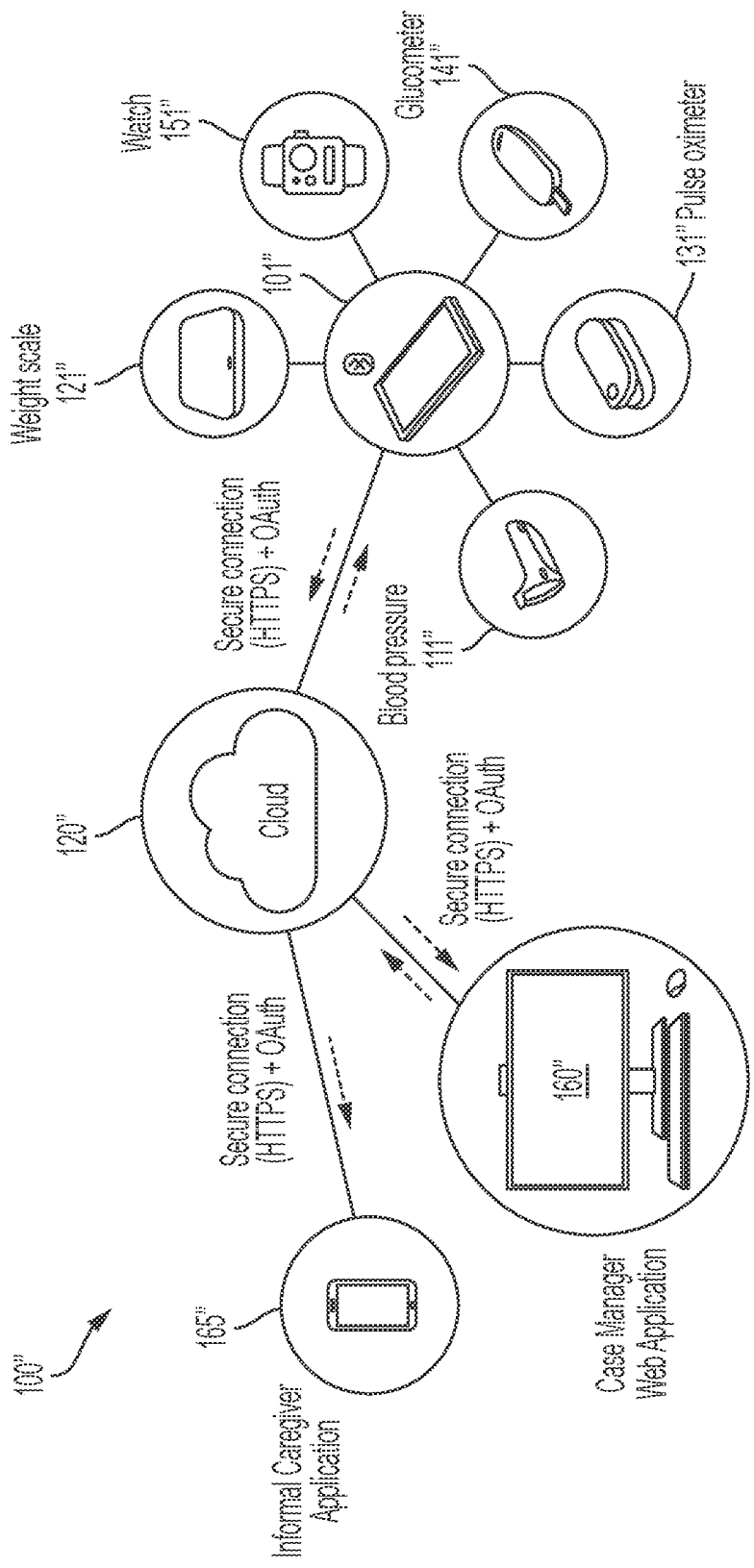
FIG. 1C depicts yet another high-level diagram of a system according to some embodiments disclosed herein.

FIG. 1C depicts yet another high-level diagram of a system according to some embodiments disclosed herein. As shown in FIG. 1C, the system includes a part 101" that is connected to a blood pressure device 111", a pulse oximeter 131", a glucometer 141", a watch 151", and a weight scale 121". Further, part 101" is connected to a cloud 120" through a secure connection. Moreover, the system of FIG. 1C also includes a case manager web application 160" and an informal caregiver application 165", each of which are also connected to cloud 120" via a secure connection.

Figure 1D:
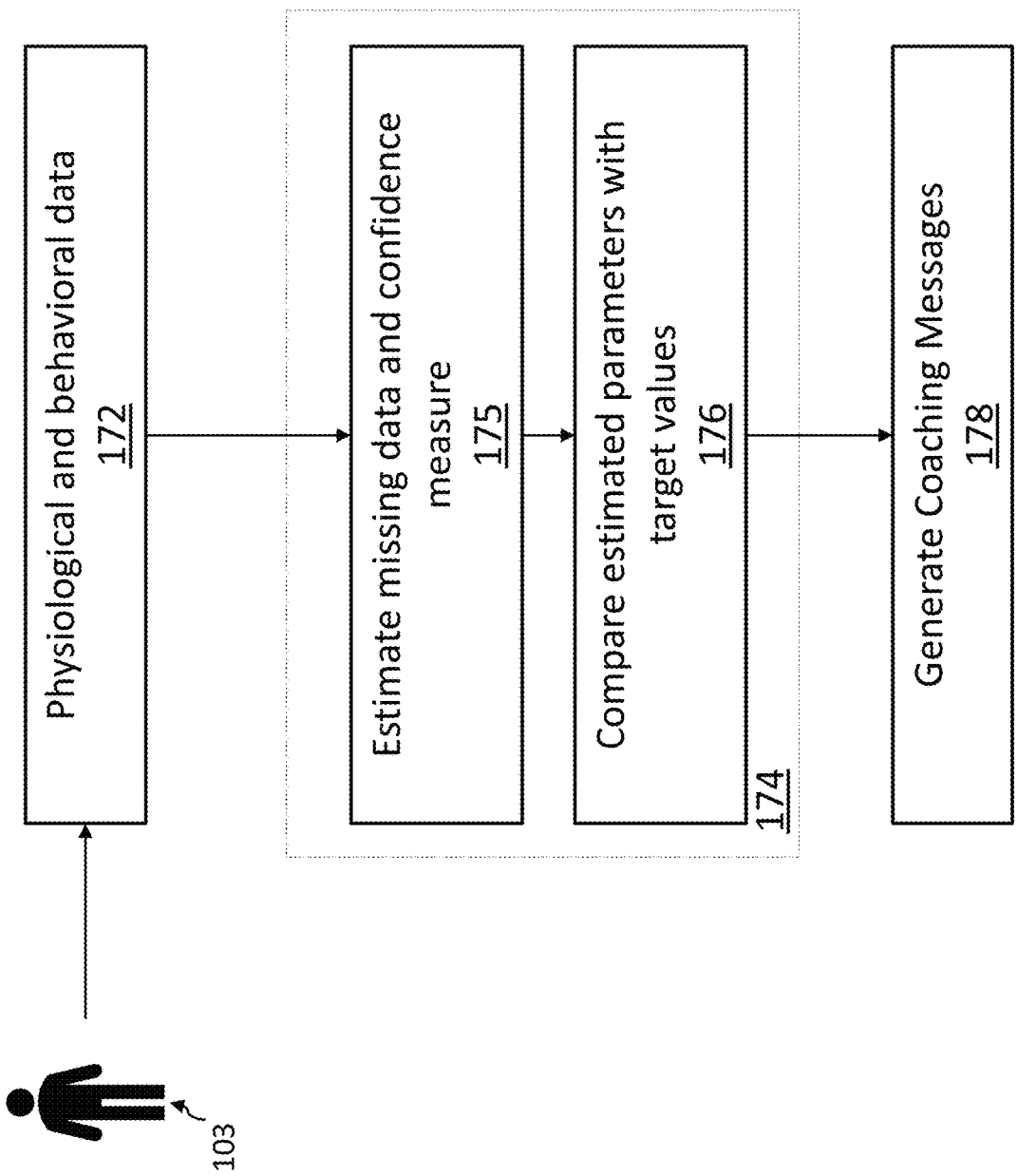
FIG. 1D is a flow chart of a method according to some embodiments.

FIG. 1D is a flow chart of a method according to some embodiments. In the flow chart, at step 172, physiological and behavioral data of a subject 103 are received. At step 175, missing data and confidence measure are estimated. At step 176, the estimated parameters are compared with target values. At step 178, coaching messages are generated.

Figure 2:
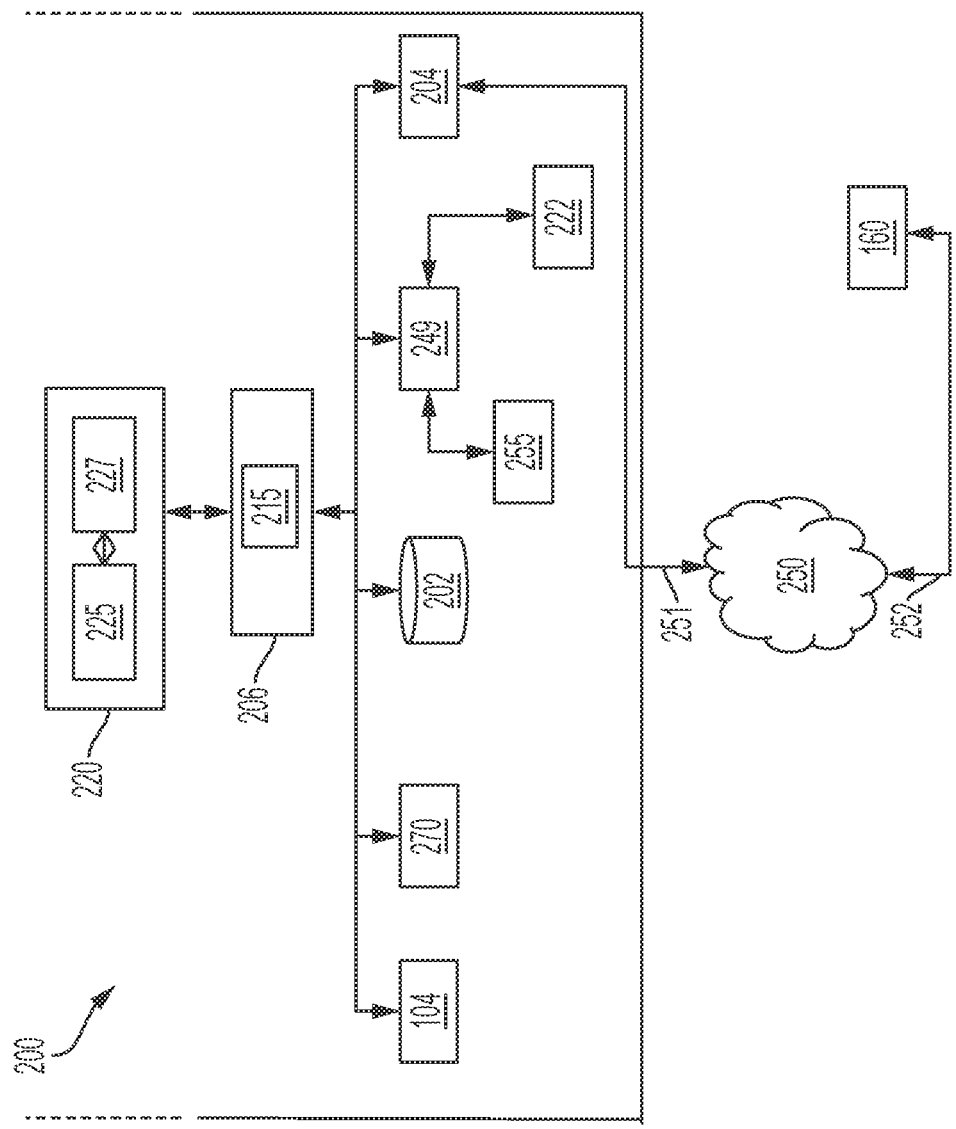
FIG. 2 depicts a high-level flow diagram of digital circuitry that can be included in a health monitor according to embodiments disclosed herein.

As noted, the health monitor 101 can comprise a processor 106. FIG. 2 depicts a high-level illustration of some of the digital circuitry that can be included in the health monitor 101. Generally, the health monitor 101 can comprise various digital electronic circuitry or computer hardware 200 that can be used with, incorporated in, or fully or partially included in the health monitor 101 according to the embodiments disclosed herein. As shown, the electric circuitry 200 can include a processor 206 that is configured to monitor the operation of the health monitor 101, send or receive signals regarding the operation of the health monitor 101, or control the operation of the health monitor 101.

The processor 206 can be configured to collect or receive information and data regarding the operation of the health monitor 101 or store or forward information and data to another entity (e.g., care provider 160 or server 120, etc.). The processor 206 can further be configured to control, monitor, or carry out various functions needed for analysis, interpretation, tracking, and reporting of information and data collected by health monitor 101. Generally, these functions can be carried out and implemented by any suitable computer system or in digital circuitry or computer hardware, and the processor 206 can implement or control the various functions and methods described herein. The processor 206 can further be generally configured to monitor the operation of the health monitor 101, send or receive signals regarding the operation of the system 200, or control the operation of the system 200.

For example, the processor 206 can be coupled to the one or more interfaces 204 of the health monitor 101 and configured to receive information regarding the physiological condition of the subject from the health monitor 101. The processor 206 can process this information to perform various functions, such as determine a health score for the subject as described above. The processor can be configured to execute instructions to perform one or more tasks in response to receiving information from the one or more interfaces 204. For example, the processor 206 can be configured to execute instructions configured to quantify severity of any undesired event (e.g., falls) detected by the interface(s) 204. In some embodiments, the processor 206 can be configured to quantify the severity of the undesired event. For example, the processor 206 can comprise instructions that can quantify undesired events.

The processor 206 can further be configured to generate a notification in response to receiving information (from the interfaces(s) 204) which can be of interest to the authorized party 160 or transmit the generated notification to the authorized party 160. The notification can be transmitted to the authorized party using any scheme known and available in the art. For example, the system 200 can be configured to transmit the notification via a communications network 250. The communications network 250 can be any communications network known and available in the art. Further, the system 200 and the processor 206 can use any means (e.g., communications links, communications protocols, etc.) known and available in the art to communicate with the authorized party 160. The system 200 can include any communications means necessary to communicate with the authorized party via the communications network 250.

In some embodiment, the authorized party 160 can be a designated device configured to receive the notification 251 generated by the health monitor 101. The designated device can be any suitable device known and available in the art. For example, the designated device can be any of a mobile device, a desktop computer, earbud, smart glasses with pop-up message window.

The third party/designated device 160 can be configured to issue a response signal 252 to the health monitor 101 in response to receiving the notification generated by the health monitor 101. The response signal 252 can comprise instructions that can be executed by the processor 206 to perform one or more tasks. For example, the one or more instructions can comprise instructions that, once executed by the processor, issue one or more alarm signals to the subject.

As noted, the health monitor 101 can be configured to generate an alarm signal in response to detection of undesired events (e.g., a fall). In some embodiments, the alarm signal generated by the health monitor 101 can be output through at least one speaker 222. The processor 206 can be coupled to the at least one speaker 222 via an input/output (I/O) interface 249 of the health monitor 101 and configured to instruct the speaker 222 to generate an alarm signal if/when an undesired event (e.g., call) is detected. The alarm signal can comprise a message in natural language.

Referring back to FIG. 2, the processor 206 can be connected to a main memory 220, and comprise a central processing unit (CPU) 215 that includes processing circuitry configured to manipulate instructions received from the main memory 220 and execute various instructions. The CPU 215 can be any suitable processing unit known in the art. For example, the CPU 215 can be a general or special purpose microprocessor, such as an application-specific instruction set processor, graphics processing unit, physics processing unit, digital signal processor, image processor, coprocessor, floating-point processor, network processor, or any other suitable processor that can be used in a digital computing circuitry. Alternatively or additionally, the processor can comprise at least one of a multi-core processor and a front-end processor.

Generally, the processor 206 and the CPU 215 can be configured to receive instructions and data from the main memory 220 (e.g., a read-only memory or a random access memory or both) and execute the instructions. The instructions and other data can be stored in the main memory 220. The processor 206 and the main memory 220 can be included in or supplemented by special purpose logic circuitry. The main memory 220 can be any suitable form of volatile memory, non-volatile memory, semi-volatile memory, or virtual memory included in machine-readable storage devices suitable for embodying data and computer program instructions. For example, the main memory 220 can comprise magnetic disks (e.g., internal or removable disks), magneto-optical disks, one or more of a semiconductor memory device (e.g., EPROM or EEPROM), flash memory, CD-ROM, or DVD-ROM disks.

The main memory 220 can comprise an operating system 225 that is configured to implement various operating system functions. For example, the operating system 225 can be responsible for controlling access to various devices, memory management, or implementing various functions of the health monitor 101. Generally, the operating system 225 can be any suitable system software that can manage computer hardware and software resources and provide common services for computer programs.

The main memory 220 can also hold application software 227. For example, the main memory 220 and application software 227 can include various computer executable instructions, application software, and data structures, such as computer executable instructions and data structures that implement various aspects of the embodiments described herein. For example, the main memory 220 and application software 227 can include computer executable instructions, application software, and data structures, such as computer executable instructions and data structures that implement the various functions of the health monitor 101, which can be employed to communicate with the subject in order to, for example, instruct the subject. Generally, the functions performed by the health monitor 102 can be implemented in digital electronic circuitry or in computer hardware that executes software, firmware, or combinations thereof. The implementation can be as a computer program product (e.g., a computer program tangibly embodied in a non-transitory machine-readable storage device) for execution by or to control the operation of a data processing apparatus (e.g., a computer, a programmable processor, or multiple computers).

The main memory 220 can also be connected to a cache unit (not shown) configured to store copies of the data from the most frequently used main memory 220. The program codes that can be used with the embodiments disclosed herein can be implemented and written in any form of programming language, including compiled or interpreted languages, and can be deployed in any form, including as a stand-alone program or as a component, module, subroutine, or other unit suitable for use in a computing environment. A computer program can be configured to be executed on a computer, or on multiple computers, at one site or distributed across multiple sites and interconnected by a communications network, such as the Internet.

The processor 206 can further be coupled to a database or data storage 202. The data storage 202 can be configured to store information and data relating to various functions and operations of the health monitor 101. For example, the data storage 202 can store the data collected by the health monitor 101. Further, in some embodiments, the database 202 can be configured to store information regarding events that may be of interest to the authorized party 160. For example, the database 202 can be configured to store the number of detected sudden acceleration or deceleration events that can indicate a fall.

The processor 206 can further be coupled to a display 270. The display 270 can be configured to receive information and instructions from the processor. The display 270 can generally be any suitable display available in the art, for example a Liquid Crystal Display (LCD) or a light emitting diode (LED) display. For example, the display 270 can be a smart or touch sensitive display that can receive instructions from a user.

The processor 206 can further be connected to various interfaces. The connection to the various interfaces can be established via a system or an input/output (I/O) interface 249 (e.g., Bluetooth, USB connector, audio interface, FireWire, interface for connecting peripheral devices, etc.). The I/O interface 249 can be directly or indirectly connected to the health monitor 101. The processor 206 can further be coupled to a communication interface 204, such as a network interface. The communication interface 204 can be a communication interface (shown in FIG. 1A) that is included in the health monitor 101 or a remote communication interface 204 that is configured to communicate with the health monitor 101. For example, the communication interface 204 can be a communications interface that is configured to provide the health monitor 101 with a connection to a suitable communications network, such as the Internet. Transmission and reception of data, information, and instructions can occur over the communications network. Further, in some embodiments, the communication interface 204 can be an interface that is configured to allow communication between the digital circuitry (e.g., a remote computer) and the health monitor 101 (e.g., via any suitable communications means such as a wired or wireless communications protocols including WIFI and Bluetooth communications schemes).

As noted, the health monitor 101 can be configured to issue instructions or alarms to the subject or the authorized party. In some embodiments, the health monitor 101 can be implemented in the electronic circuitry of the health monitor 101, for example in application software 227, and configured such that one or more instructions or alerts can be stored in the form of instructions or audio files (e.g., in the form of Waveform Audio File Format) in the main memory 220. The health monitor 101 can be configured such that upon initialization of the health monitor 101, the processor 206 transfers audio files for instructing the subject or issuing alerts from the main memory 220 and causes the execution of the files. The subject instruction system can communicate, via the I/O interface 249, with the one or more speakers 22 of the health monitor 101, and instruct the speakers 222 to play the relevant audio files for the subject.

The verbal communication with the subject can be conducted using natural language. Additionally or alternatively, the verbal communication with the test subject can be performed by using one or more pre-recorded messages configured for delivery to the test subject. The pre-recorded messages can be stored in the database 202 and accessed by the processor 206 as needed. The processor 206 can use the audio speaker 222 to conduct verbal communication with the subject. In some embodiments, the health monitor 101 can include a microphone for receiving commands, instructions, or requests from the subject or caregiver.

In some embodiments, the health monitor 101 can further comprise an interface 255 configured to receive information from the subject or the caregiver. The interface 255 can be coupled to the I/O interface 249 of the system 200 such that information received by the interface 255 are directed, through the I/O interface 249 to the processor 206. Similarly, the interface 255 can be configured to receive instructions from the processor 206 through the I/O interface 249.

Additionally or alternatively, the health monitor 101 can include Bluetooth capabilities for communication to other wearable or non-wearable systems, Global Positioning System (GPS) for sensing the location of the subject, one or more accelerometers for detecting the activity of the subject, one or more gyroscopes for detection of body posture of the subject, a red and infrared LED and a photodiode for heart rate measurement and reflective plethysmography to measure the blood oxygenation, an altimeter and pressure sensor, a temperature sensor, or a battery charger system. Further, in some embodiments, the health monitor 101 can comprise a rechargeable battery.

In some embodiments, the health monitor 101 can be coupled with other wearables. The subject can use other wearables once in a while for a specific time interval. For example, a subject with hypertension can wear the blood pressure monitor over predetermined intervals (e.g., six months) for a few days to obtain blood pressure measurements over predetermined time periods (e.g., every hour). Alternatively or additionally, other wearables such as a waist wearable can be used over predetermined intervals (e.g., six months) for a few days for gait and balance assessment of the patient. Similarly, a wearable ECG patch can be used over predetermined intervals (e.g., six months) for assessment of the cardiac rhythms of the patient.

For example, as shown in FIG. 1B, in some embodiments, the health monitor 101 can include or be coupled with a wearable patch 131 that is disposed on the subject's body (e.g., the subject's chest). The patch 131 can comprise a chest strap or adhesive having at least one of a processing unit and memory, 1 lead ECG, accelerometer, gyroscope for posture detection, Bluetooth capabilities to communicate with the health monitor 101, a rechargeable battery, or a battery charger module.

Further, as also shown in FIG. 1B, in some embodiments, the health monitor 101 can include or be coupled with a wearable 111 (e.g., worn around the waist) that can be worn in any suitable manner, for example with a belt. The wearable 111 can comprise a processing unit and memory, an accelerometer, a gyroscope, Bluetooth capabilities for communicating with the health monitor 101, a rechargeable battery, or a battery charger module.

Still further, as also shown in FIG. 1B, in some embodiments, the health monitor 101 can include or be coupled with a wearable 121 (e.g., worn around the arm) that can comprise a processing unit and memory, an Oscillometric blood pressure measurement module, an inflatable cuff, Bluetooth capabilities for communicating with the health monitor 101, a rechargeable battery, or a battery charger module.

Figure 3:
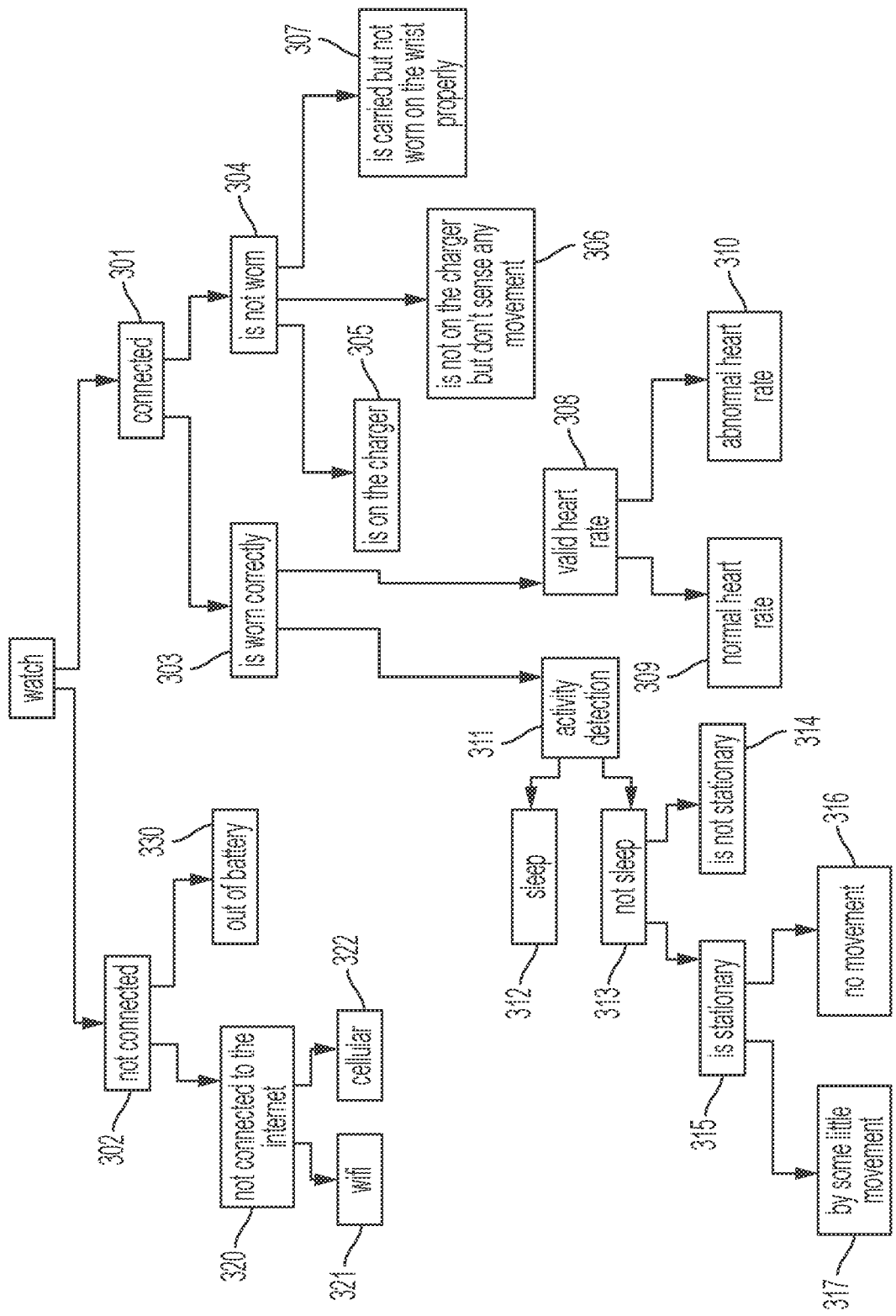
FIG. 3 is a flow diagram of example procedures that can be executed in a health monitor according to embodiments disclosed herein.

FIG. 3 is a flow diagram of example procedures that can be executed in a health monitor according to embodiments disclosed herein. As shown, the health monitor 101 (e.g., a wearable watch) can determine whether the device is connected 301 or not connected 302. If the device is connected 301, the health monitor can determine whether the device is worn 303 or not worn 304. If the device is not worn 304, the wearable can determine whether the device is on the charger 305, is not on the charger and no movement is sensed 306, or is carried but not worn on the wrist properly 307.

If the device is worn correctly 303, the device can determine whether the subject has a valid heart rate 308. If a valid heart rate is detected 308, the device can determine whether the heart rate is normal 309 or abnormal 310. Lack of heart rate 308 or presence of an abnormal heart rate 310 can trigger an alarm to a care provider.

If the device is worn correctly 303, the device can determine whether the subject is moving 311. Specifically, the device can determine whether the subject is sleeping 312 or not sleeping 313. If the subject is not sleeping 313, the device can determine if the subject is not stationary 314 or stationary 315. If the subject is stationary 315, the device can determine if the subject is moving 317 or if there is no movement 316. Each of these situations can trigger an appropriate alarm or lead to collection of relevant data.

If the device is not connected 302, the health monitor can determine whether it is out of battery 330 or whether the device is not connected to the communications network (e.g., Internet) 320. If no network connection is detected 320, the health monitor can attempt to connect to an alternate communications network (e.g., via cellular 322 or Wi-Fi 321).

Figure 4:
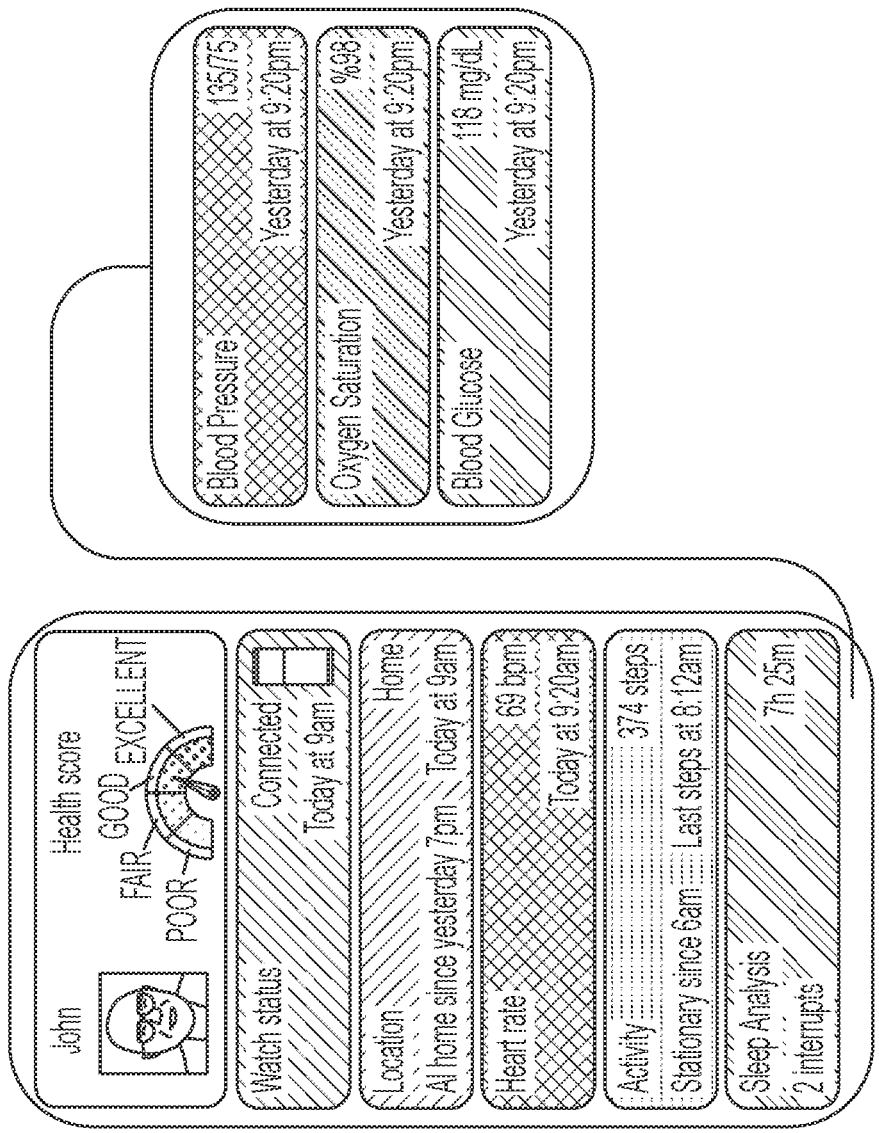
FIG. 4 is an illustrative example of a visual interface of a health monitor according to embodiments disclosed herein.

FIG. 4 is an illustrative example of a visual interface of a health monitor according to embodiments disclosed herein. As shown, the health monitor can receive information such as blood pressure, blood oxygen saturation level, and blood glucose level of the subject from connected interfaces, systems, or sensors. The visual interface can display (to the caregiver or authorized party or to the subject) information such as the status of the wearable (battery level, connectivity, etc.), location of the subject, heart rate of the subject, activity level of the subject, or sleep analysis for the subject.

Figure 5:
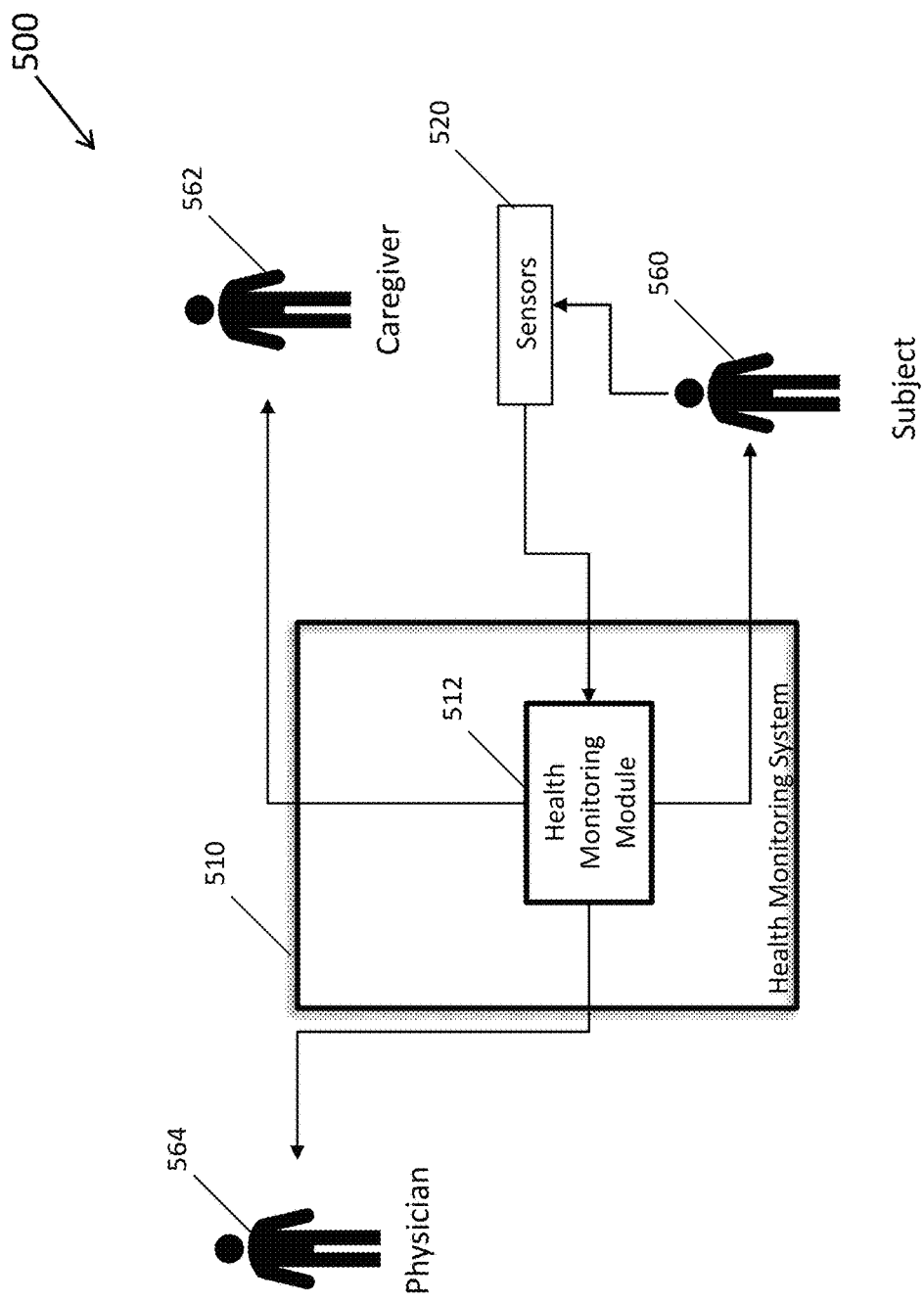
FIG. 5 is a high level block diagram of a health monitoring system according to some embodiments.

FIG. 5 is a high level block diagram of a health monitoring system 500 according to some embodiments. System 500 includes a health monitoring system 510 and one or more sensors 520. Further, health monitoring system 510 includes a health monitoring module 512. As shown in FIG. 5, health monitoring system 500 may communicate with one or more health operators. The one or more health operators may include, for example, a subject 560 and one or more health actors, such as a caregiver 562 or a physician 564.

In some embodiments, health monitoring system 510 collects physiological and behavioral data using sensors 520. Moreover, health monitoring system 510 may collect manual data input by subject 560 and may provide coaching recommendations to the subject. The system may also process real time and historical data to detect important events that may require intervention, and alert one or more health actors such as caregiver 562 or physician 564.

Figure 6:
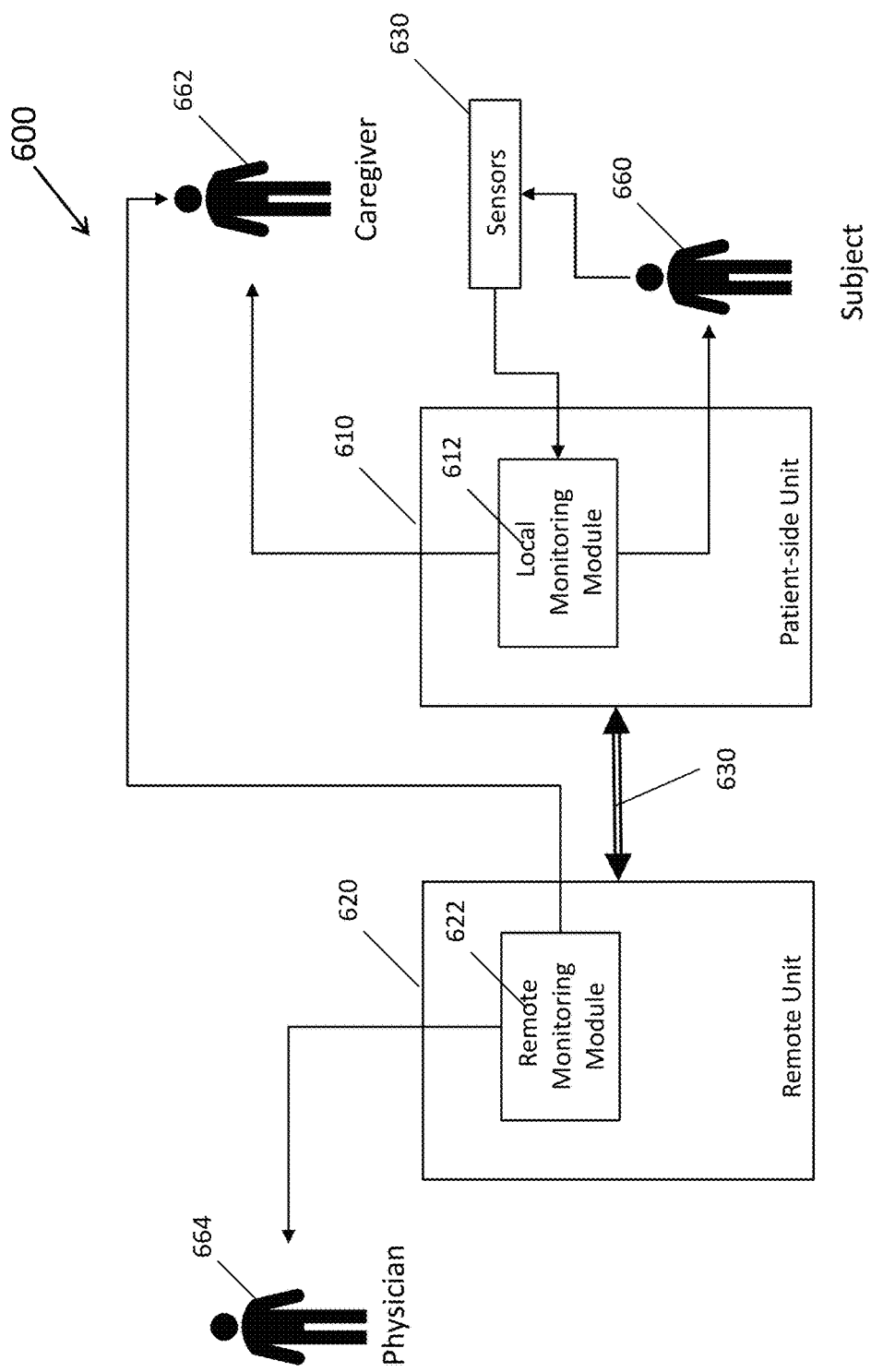
FIG. 6 is a high level block diagram of a health monitoring system according to some other embodiments.

FIG. 6 is a high level block diagram of a health monitoring system 600 according to some other embodiments. System 600 includes a patient side unit 610, a remote unit 620, and one or more sensors 630. Moreover, patient side unit 610 includes a local monitoring module 612, and remote unit 620 includes a remote monitoring module 622. Further, patient side unit 610 and remote unit 620 may communicate with each other through a channel 630. Channel 630 may include one or more types of communication channels such as wireless connections, Internet connections, telephone connections, etc.

Patient side unit 610 may be designed to communicate with sensors 630. Moreover, patient side unit 610 may communicate with one or more health operators such as a subject 660, a caregiver 662, or a physician 664. Moreover, patient side unit 610 may perform real-time and time-sensitive tasks such as detection of events and generation of alarms. Patient side units 610 may communicate the alarms to caregiver 662 or other health operators. Also, patient side unit 610 may communicate to remote unit 620 through channel 630 a subset of data received from sensors 630 or other information such as the alarms or they detected events.

Remote unit 620, on the other hand, may be designed to perform less time-sensitive tasks on a regular basis. These tasks may include, for example calculation of risks and determination of the state of the diseases of subject 660.

Figure 7:
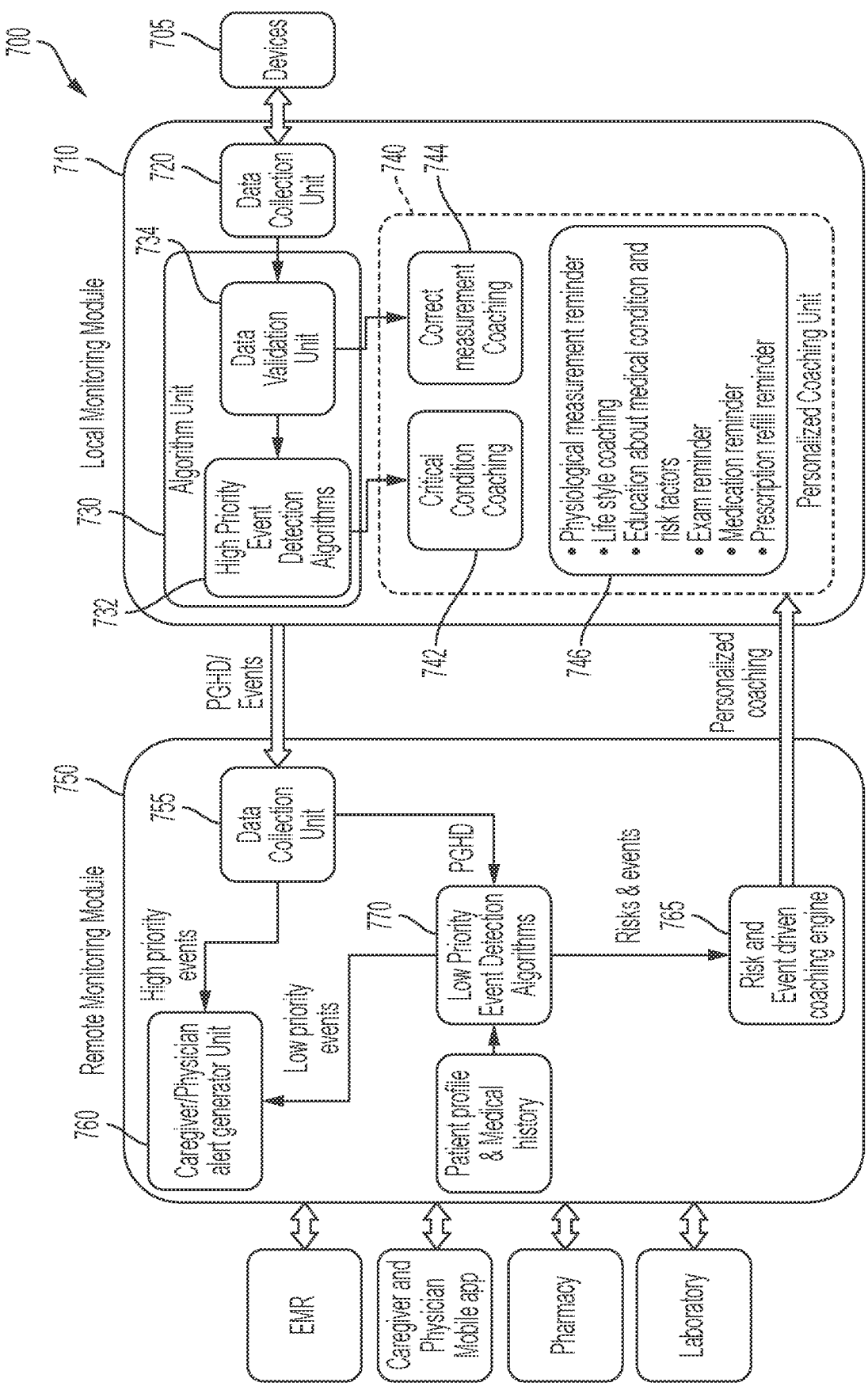
FIG. 7 is a block diagram of the health monitoring system according to yet another embodiment.

FIG. 7 is a block diagram of a health monitoring system 700 according to yet another embodiment. System 700 includes one or more devices 705, a local monitoring module 710, and a remote monitoring module 750.

In various embodiments, devices 705 may include a wearable or a non-wearable measurement device that may perform some measurements, and collect physiological or behavioral data from a subject. The measurements may include, for example, a blood pressure measurement, a blood glucose measurement, a heart rate measurement, oxygen saturation, body temperature, electrocardiogram, body movements, number of steps, sleep hours, location, mobility, etc. Further, the device may include one or more sensors, processing units, or user interfaces. Some examples of such devices include a smart watch, an ECG patch, a blood pressure measurement device, a glucose measurement device, etc.

Local monitoring module 710 includes a local data collection unit 720, a local event detection unit 730, and a local coaching unit 740.

Local data collection unit 720 may collect physiological or behavioral data as measured by devices 705 from, for example, a subject. Local data collection unit 720 may further communicate with the devices, and initiate a new measurement or change the sampling frequency of a measurement according to the subject's condition and validity of the collected data. For example, when there is a recording of a very low or very high heart rate of a subject, local data collection unit 720 may increase the frequency of the heart rate measurement to have a clearer picture of the subject's condition. As another example, when there is a significant change in the location of a subject with Alzheimer disease, the local data collection unit may increase the frequency of location sampling so that the caregiver has the real-time tracking of the location of the subject.

Local event detection unit 730, on the other hand, may process the collected data to determine the reliability of the measurements, or detect high priority events that may require timely intervention. In particular, local event detection unit 730 includes a local high priority event detection unit 732 and a local data validation unit 734.

Local data validation unit 734 may calculate the reliability of the data collected during the measurements. In determining the reliability, local data validation unit 734 may use one or more factors such as the quality of the raw data from devices, subject's motion during measurement, user activities before measurement, timing of the measurement, body posture and deviation of the measurement from expected values based on patient historical data and medical history, etc. Local data validation unit 734 may label data based on a reliability measure.

Local high priority event detection unit 732, on the other hand, may detect high priority events that may require timely intervention. These events may include instances where data resulting from some physiological measurements are within emergency range. For example, when the measurements indicate one or more of the following data: a systolic blood pressure above 180 mmHg, a diastolic blood pressure above 120 mmHG, a blood glucose level above 300 mg/dL or below 70 mg/dL, a blood oxygenation below %90, etc. Local high priority event detection unit 732 may compare the data with default thresholds or with customized thresholds set by the subject's physician or caregiver and may determine whether the measurements are in the critical range. The events may also include critical behavioral conditions like lack of movement for a long period of time (like 4 hours) when the subject is expected to be awake based on historical data or rapid downward movement of the body that may indicate a fall.

Local coaching unit 740, may provide coaching messages to the subject. Local coaching unit 740 includes a critical condition coaching unit 742, a correct measurement coaching unit 744, and a noncritical coaching unit 746.

Critical condition coaching unit 742 may provide coaching messages when there is a critical event detected by local high priority event detection unit 732. The coaching message may include recommendations to the subject for managing a critical condition. For example, in case of high systolic blood pressure above 180 or high diastolic blood pressure of 120, the coaching message may recommend the subject to call 911 if the subject is experiencing any other associated symptoms of target organ damage such as chest pain, shortness of breath, back pain, numbness/weakness, change in vision, or difficulty. As another example in case of very low blood glucose level below 70 mg/dL, the coaching message may recommend the subject to eat something that has about 15 grams of carbohydrates, wait about 15 minutes, and measure again.

Correct measurement coaching unit 744 may provide coaching messages to the subject when local data validation unit 734 detects that a measurement is not reliable. For example, when a blood pressure measurement is detected to be unreliable, the coaching message may recommend the subject to follow the correct blood pressure measurement method like resting for 5 minutes, not moving during the measurement, and repeating the measurement.

Noncritical coaching unit 746 may provide lower priority coaching recommendations to the subject for long term prevention and management of the disease. These messages may be personalized coaching messages that are composed by remote coaching unit 765 and sent to local monitoring module 710. The recommendations may include physiological measurement types and frequency, laboratory tests reminder, lifestyle recommendations, diet recommendations, activity, stress reduction techniques, etc.

The coaching messages may include, for example, messages regarding correct measurement method when a measurement is detected to be unreliable; messages regarding critical events that may be detected by the algorithm unit; or messages regarding the prevention and management of the diseases. The messages may also include questions regarding symptoms of the subject when a critical event is detected.

Remote monitoring module 750 includes a remote data collection unit 755, an alert generator unit 760, a remote coaching unit 765, and a remote event detection unit 770.

Remote data collection unit 755 may receive data and events from one or more subjects, authenticate user data, separate events and data, and store the data in a database.

Alert generator unit 760 may be triggered by the events received from the local monitoring module and generate alert messages to one or more health factors interacting whether the one or more subjects for proper intervention.

Remote event detection unit 770 may process the data and calculate the risks and state of the disease for the one or more subjects on a regular basis, such as daily or weekly, based on the collected data, patient profiles, or medical history of the subjects. It may also categorize individuals to high risk and low risk groups for getting the diseases in the future and determine whether the disease is controlled or uncontrolled state.

Remote coaching unit 765 may provide personalized coaching recommendations according to the risks and state of the diseases of a subject. The recommendations may include physiological measurement types and frequency, laboratory tests reminder, lifestyle recommendations, diet recommendations, activity, stress reduction techniques and etc.

As shown in FIG. 7, remote monitoring module 750 may interact with an external electronic medical record (EMR), Pharmacy and Laboratory to access subject's medical history, diagnoses, medications, immunization dates, allergies, lab results and doctor's notes, etc.

Figure 8:
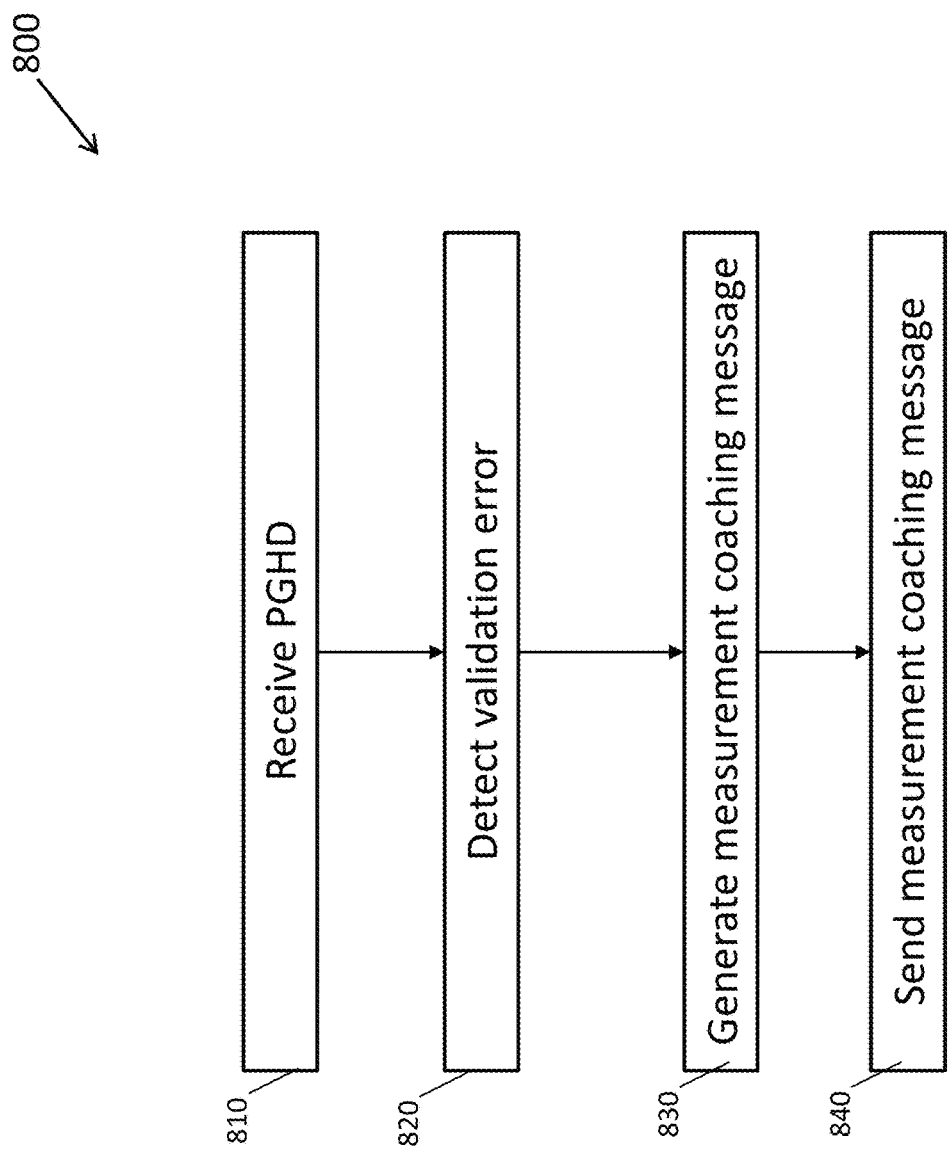
FIG. 8 is flow chart of a coaching process performed by a local monitoring module according to some embodiments.

FIG. 8 is flow chart of a coaching process 800 performed by a local monitoring module according to some embodiments.

More specifically, at step 810, the module may you receive PGHD, as described above.

At step 820, the module may detect a validation error based on which, at step 830, the module may generate measurement coaching messages.

At step 840, the module may send the measurement coaching messages to the patient or to a caregiver to address the validation errors.

Figure 9:
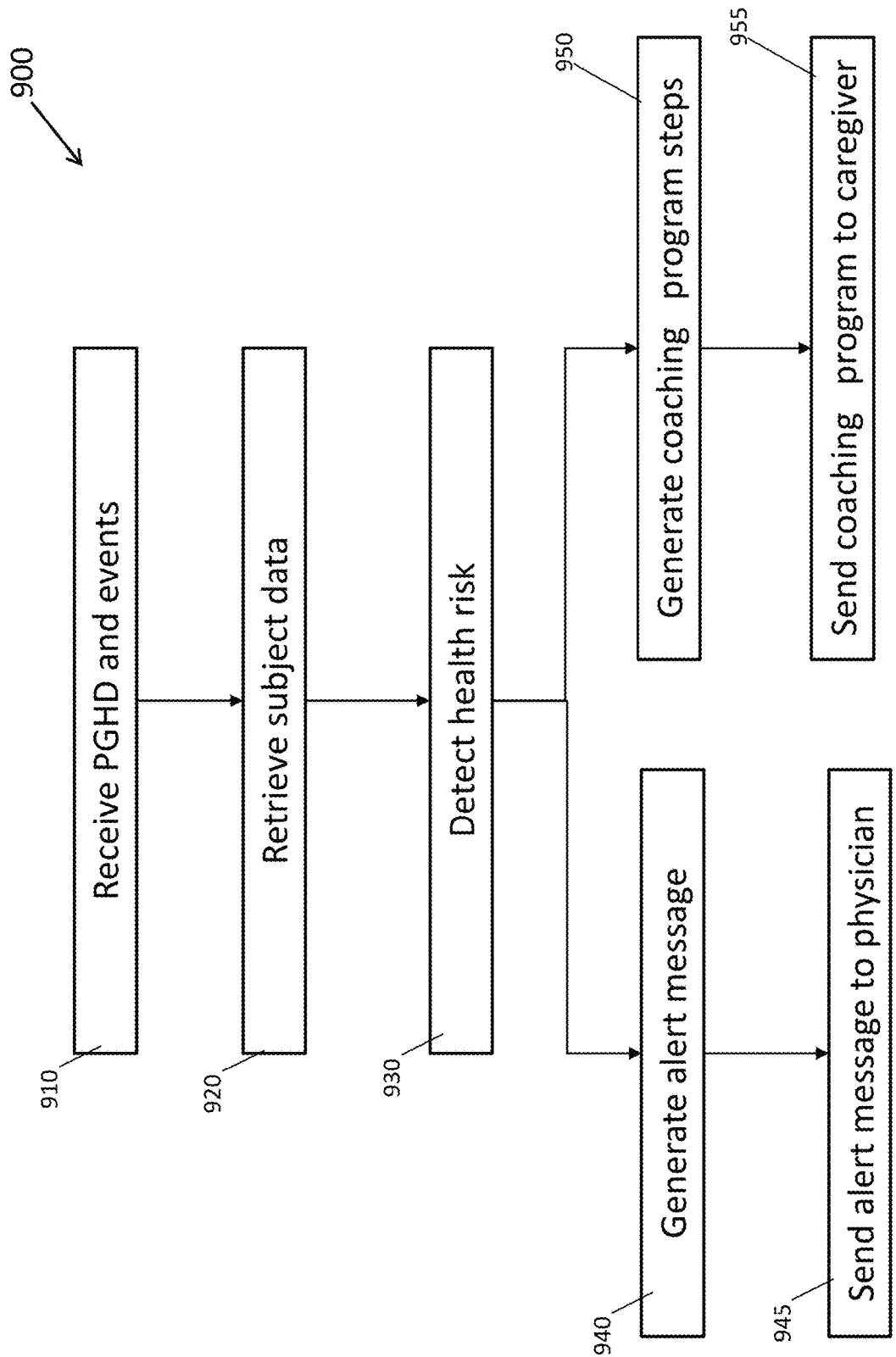
FIG. 9 is a flow chart of a coaching and alerting process performed by a remote monitoring module according to some embodiments.

FIG. 9 is a flow chart of a coaching and alerting process 900 performed by a remote monitoring module according to some embodiments.

In particular, at step 910, the module may receive PGHD and events. At step 920, the module may retrieve subject data.

At step 930, based on the above information, the module may detect a health risk. Based on the detected health risk, at step 940, the module may generate alert messages and at step 945 send those alert messages to a physician to trigger appropriate responses to the health risk.

Alternatively, or in parallel, to steps 940 and 945, based on the health risk the module may generate coaching program steps at step 950 of the process 900. Further, the module may send the coaching program to a caregiver of the patient to address the health risk.

Figure 10:
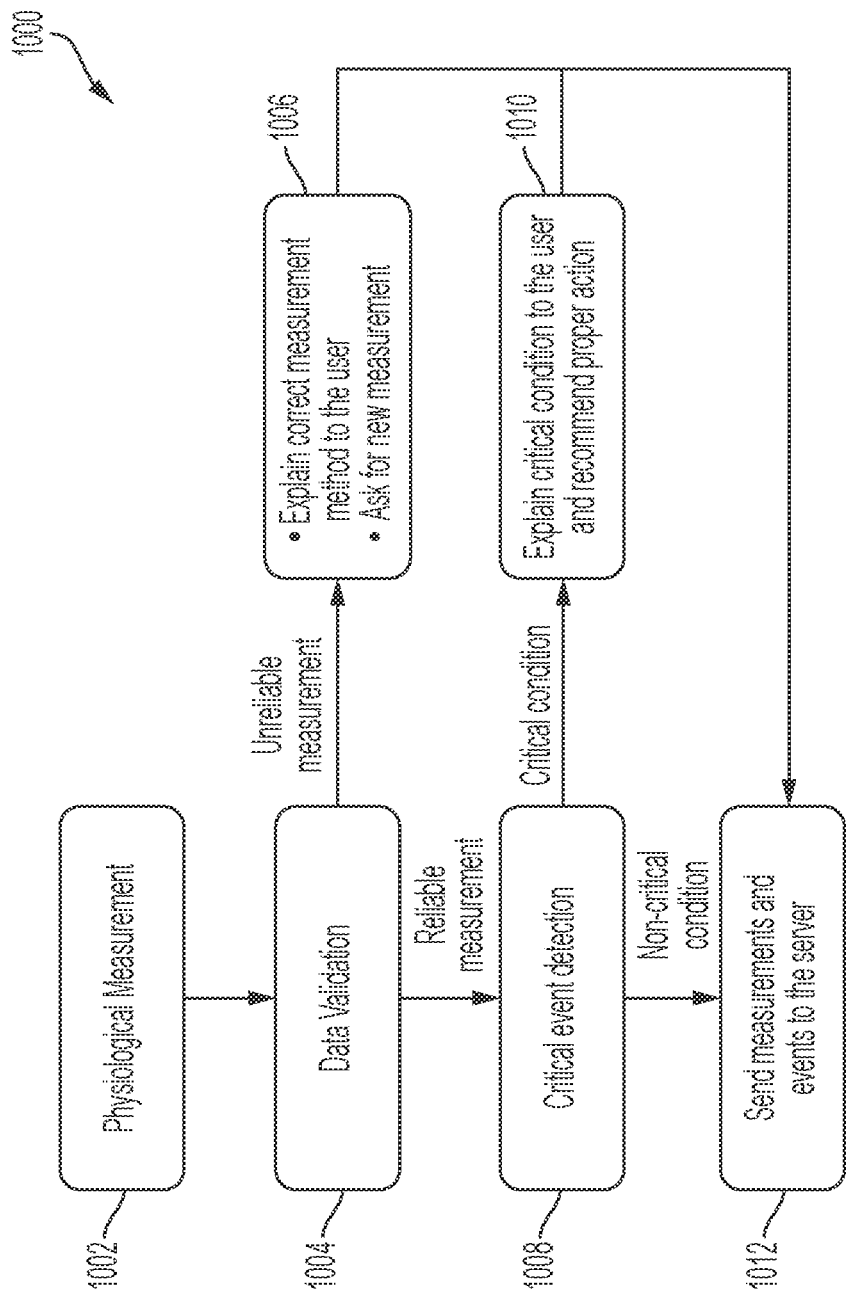
FIG. 10 is a flowchart for a coaching process performed by a local monitoring module according to another embodiment.

FIG. 10 is a flowchart 1000 for a coaching process performed by a local monitoring module according to another embodiment. As shown in Flowchart 1000, in step 1002, some measurements are performed by one or more sensors and sent to the data validation module.

Further, in step 1004, the data validation module evaluates the reliability of the collected measurements.

When the collected measurements are not reliable, in step 1006, the local coaching unit provides coaching recommendations to the subject for performing a correct measurement and guide the subject to re-do a measurement in a reliable fashion.

When, on the other hand, the collected measurements are reliable, the local event detection unit may detect a critical event in step 1008.

When such a critical event is detected, in step 1010, the local coaching unit may provide some related critical condition coaching or recommend proper actions to the subject or to the health actors.

In step 1012, the local monitoring module may send a subset, and in some cases all of, the reliable measurements or the unreliable measurements to the server for further processing.

Figure 11:
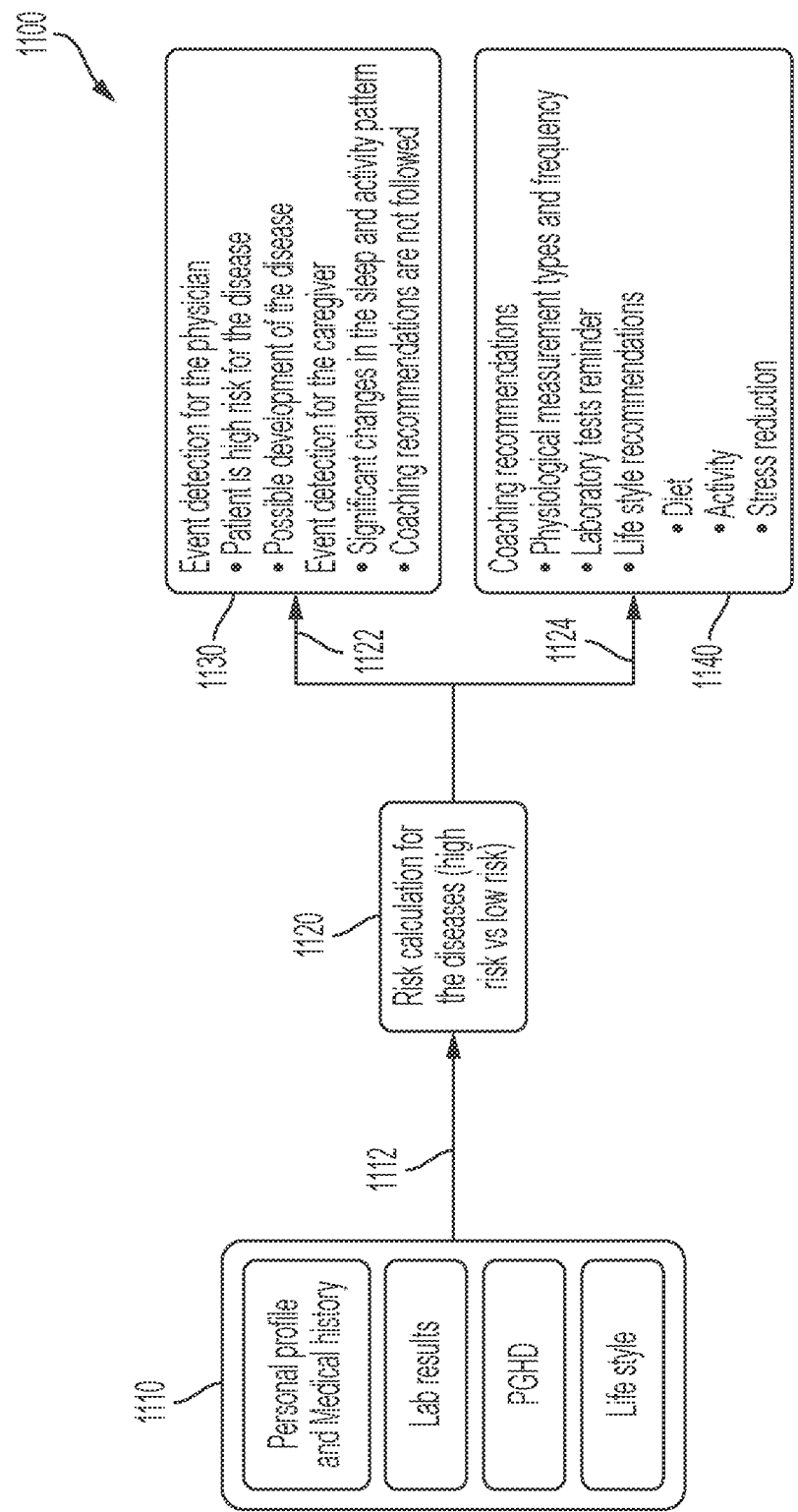
FIG. 11 is a block diagram for a disease prevention process performed by a remote monitoring module according to some embodiments.

FIG. 11 is a block diagram for a disease prevention process 1100 performed by a remote monitoring module according to some embodiments. Disease prevention process 1100 includes a medical record block 1110, a risk calculation block 1120, an event detection block 1130, and a coaching recommendation block 1140. Moreover, process 1100 includes steps 1112, 1122, and 1124, explained below.

In step 1112, risk calculation block 1120 receives one or more medical record data from medical record block 1110. The medical record data may include one or more of personal profile and medical history of the subject, lab results, PGHD, or relevant lifestyle information related to the subject.

Based on the received medical record data, risk calculation block 1120 may calculate a risk level for one or more diseases for the subject. In some embodiments, the calculated risk level may be categorized as high or low, or based on some other risk scale.

In step 1122, risk calculation block 1120 sends to event detection block 1130 information based on the calculated risks. This information may indicate, for example, that the subject is at high risk for developing a disease.

Based on the information received at step 1122, event detection block 1130 may generate and send one or more alerts to one or more health operators. For example, the event detection block may send an alert to a physician of the subject. This alert may indicate that, for example, the patient is at a high risk for a disease or a development in the disease is possible. Alternatively, or in addition, the event detection block may send an alert to a caregiver of the subject. This alert may, for example, recommend some changes in the sleep or activities of the subject, or inform that the coaching recommendations have not been followed.

Moreover, in step 1124, risk calculation block 1120 sends to coaching recommendation block 1140 information based on the calculated risks. This information may indicate, for example, that the subject is at a low risk for developing the disease.

Coaching recommendation block 1140 may generate one or more coaching recommendations based on the information received at step 1124 and possibly other information such as historical trend. The coaching recommendation block may send those coaching recommendations to one or more health operators, such as the subject or the caregiver of the subject. The coaching recommendations may relate, for example, to recommended physiological measurement types and frequencies, laboratory test reminders, or lifestyle recommendations such as diet, activities, or stress reduction.

Figure 12:
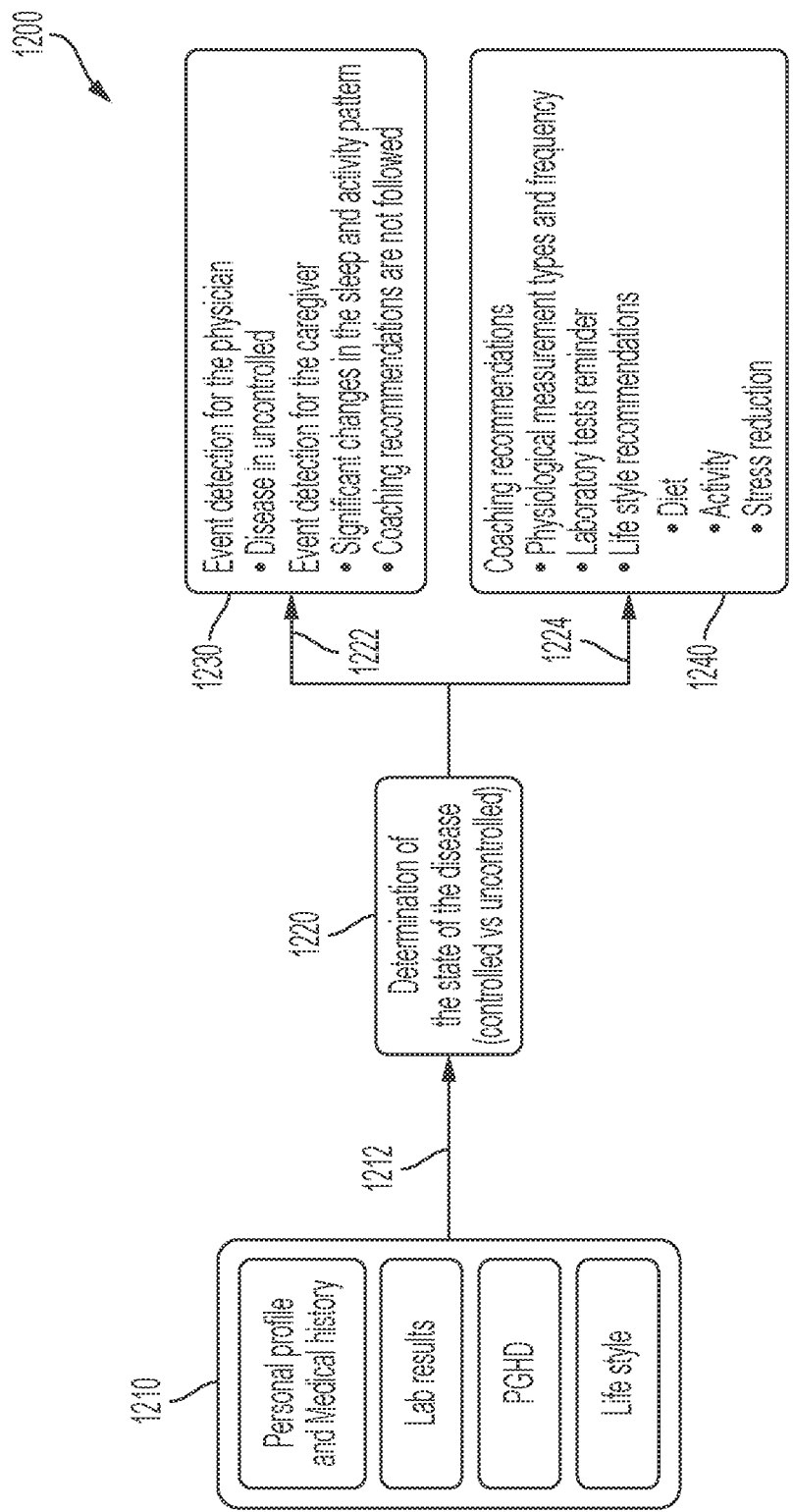
FIG. 12 is a block diagram for a disease management process performed by the remote monitoring module according to some embodiments.

FIG. 12 is a block diagram for a disease management process 1200 performed by the remote monitoring module according to some embodiments. Disease management process 1200 includes a medical record block 1210, a disease state determination block 1220, an event detection block 1230, and a coaching recommendation block 1240. Moreover, process 1200 includes steps 1212, 1222, and 1224, explained below.

In step 1212, disease state determination block 1220 receives one or more medical record data from medical record block 1210. Based on the received medical record data, disease state determination block 1220 may determine a state of a disease of the subject. In Some embodiments, the disease state determination block may determine the disease to be in a controlled state or in an uncontrolled state.

In step 1222, disease state determination block 1220 sends to event detection block 1230 information based on the determined state. This information may indicate, for example, that the disease is in an uncontrolled state.

Based on the information received at step 1222, event detection block 1230 may generate and send one or more alerts to one or more health operators. For example, the event detection block may send an alert to a physician of the subject. This alert may indicate, for example, the uncontrolled state of the disease. Alternatively, or in addition, the event detection block may send an alert to a caregiver of the subject. This alert may, for example, recommend some changes in the sleep or activities of the subject, or inform that the coaching recommendations have not been followed.

Moreover, in step 1224, disease state determination block 1220 sends to coaching recommendation block 1240 information based on the determined state. This information may indicate, for example, that the disease is in a controlled state.

Coaching recommendation block 1240 may generate one or more coaching recommendations based on the information received at step 1224 and possibly other information such as historical trend. The coaching recommendation block may send those coaching recommendations to one or more health operators, such as the subject or the caregiver of the subject. The coaching recommendations may relate, for example, to recommended physiological measurement types and frequencies, laboratory test reminders, or lifestyle recommendations such as diet, activities, or stress reduction.

Figure 13:
FIG. 13 shows an exemplary scoring table for calculating disease risk as utilized by the remote monitoring module according to some embodiments.

FIG. 13 shows an exemplary scoring table 1300 for calculating disease risk as utilized by remote monitoring module according to some embodiments. The example shows the risk calculation method for development of hypertension in a subject based on different risk factors. The overall score determines the risk of developing hypertension in a subject.

Figure 14:
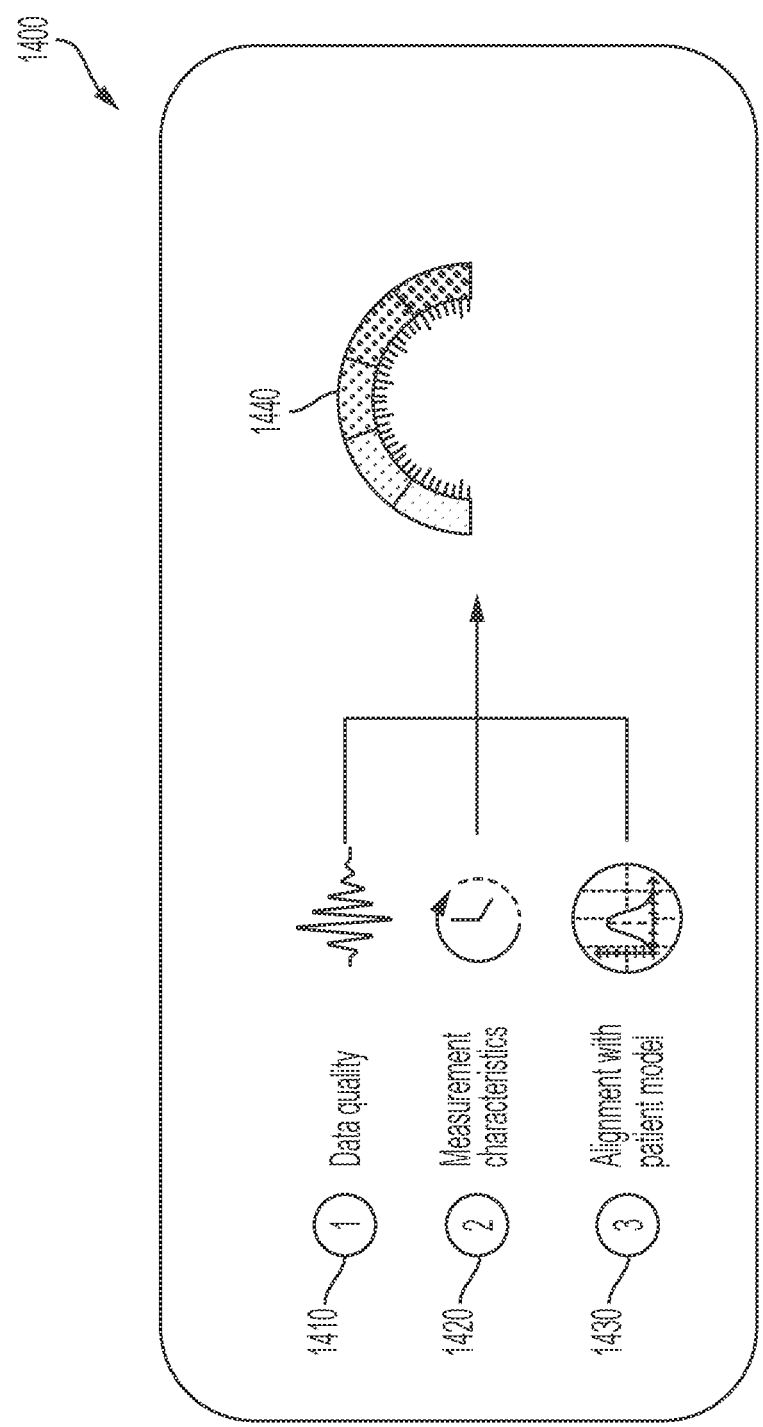
FIG. 14 illustrates a data assessment mechanism 1400 according to some such embodiments.

Some embodiments utilize data assessment mechanisms that minimize sources of data noise and help remove false positives and further help drive better control for a health issue such as hypertension. FIG. 14 illustrates a data assessment mechanism 1400 according to some such embodiments. In various embodiments, mechanism 1400 may be utilized by a health monitoring system, or one or more modules in a health monitoring system.

Mechanism 1400 uses one or more of three factors to determine the reliability of a measurement. In particular, mechanism 1400 may use one or more of a data quality factor 1410, a measurement characteristics factor 1420, and an alignment factor 1430. Based on these factors, data assessment mechanism 1400 may generate a total confidence factor 1440.

Figure 15:
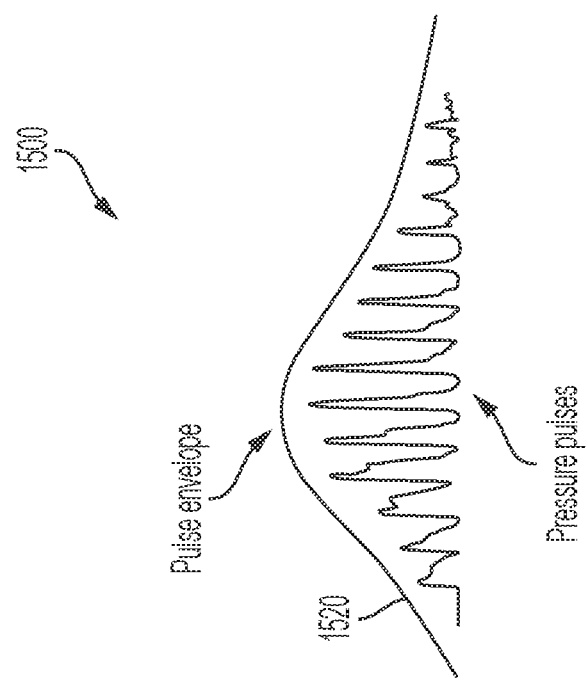
FIG. 15 illustrates a data quality measurement mechanism 1500 for determining data quality factor 1410 according to one embodiment.
Figure 15:
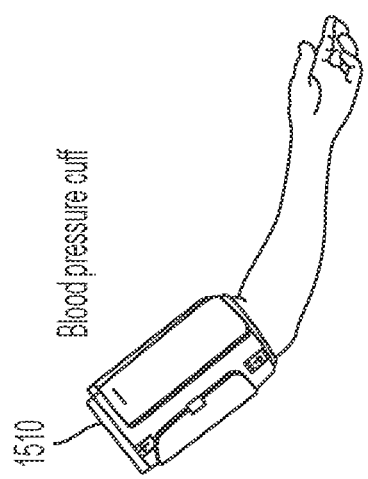

FIG. 15 illustrates a data quality measurement mechanism 1500 for determining data quality factor 1410 according to one embodiment. In various embodiments, mechanism 1500 may be utilized by a health monitoring system, or one or more modules in a health monitoring system.

In particular, data quality measurements mechanism 1500 uses data 1520 collected by a measurement system 1510 to determine a raw data quality confidence factor, abbreviated to raw confidence factor, $C_{raw}$. In the example of FIG. 15, mechanism 1500 corresponds to determining the quality of blood pressure measurements, measurement system 1510 is a blood pressure cuff system, and raw data 1520 corresponds to various characteristics of the blood pressure pulses recorded by the blood pressure cuff system. Other examples may include ECG signals for detecting arrhythmias or pulse waveforms from photoplethysmography devices used to measure heart rate and oxygen saturation.

In some embodiments, the raw confidence factor is a number between 0 and 1. In the case of blood pressure raw data 1520 in FIG. 15, the raw confidence factor $C_{raw}$ may be calculated based on different features such as the features discussed below. While the following features are discussed for the example of pulse signals, they may also be applied to other types of health related data.

A first feature may be the regularity of the consecutive pulse intervals. In some embodiments, the regularity may be calculated as the variance of the pulse intervals normalized by the average of the pulse intervals. In some embodiments, the normalized variance should be less than a threshold value for a reliable measurement. Larger values may for the variance may indicate a less reliable measurement.

As a second feature, the morphology of the pulse waveforms and their variation across different pulses may be used as a criterion for reliability of a measurement. In some embodiments, pulse morphologies should not vary significantly after normalizing the height of the pulses in a reliable measurement. In some embodiments, the morphology of the pulse waveforms may be quantified based on some features of the pulse waves such as width at half height and rise time along with their variation across different pulses. For example, in some embodiments, the variance of the pulse widths at half height normalized by the average pulse widths should be smaller than a threshold value (for example 0.1, 0.2, 0.25, etc.). The larger value of the variance indicates the lower reliability of the measurement As a third feature, the morphology of pulse envelope may be used as a criterion for reliability of a measurement. In some embodiments, the pulse envelope should have a bell shape. In some embodiments, a quantitative parameter $\propto$, called Gaussian morphology variance (hereinafter gmv), may be calculated to determine the degree of deviation of the pulse envelope from the Gaussian. As a first step, a Gaussian function may be fitted to the pulse envelope. Then, the gmv may be calculated as the sum of the absolute difference between the samples of the fitted curve and the samples of the actuals pulse envelope waveform normalized by the sum of samples of the fitted curve as detailed in Eq. (1), $$\propto = \frac{\sum_{i=1}^{N} |G_i - Env_i|}{\sum_{i=1}^{N} G_i} \quad (1)$$

in which $G_i$ represents the samples of the fitted Gaussian function and $Env_i$ represents the samples of the pulse envelope curve.

In Eq. (1), the value of the gmv $\propto$ may be used as a criterion for the reliability of the measurement. A larger value for the gmv may indicate a less reliable measurement.

In some embodiments, one of the above listed features or an average of two or all three of them may be used to determine the raw data confidence factor.

In some embodiments, measurement characteristics factor 1420 may be based on various characteristics of the process during which the raw data were collected. These characteristics may include, for example, possible movements of the subject in a period before or during the time that the raw data were collected. For example, extensive or intense activities by the subject before the collection may result in changing the subject's physical status from her normal state to an agitated state in which, for example, her blood pressure is above her normal blood pressure. Alternatively, if the subject moves during collection of the raw data, the movement may create motion artifacts and introduce errors in the measurement.

In various embodiments, measurement characteristics factor 1420 may be measured using measurement mechanisms such as accelerometers or pedometers included in a mobile device such as a wearable device or in the measurement system such as the blood pressure cuff. The measurement characteristics data such as the amount of movement during the measurements and the amount of activity prior to the raw data collection may be combined into a behavior confidence factor $C_{beh}$.

In some embodiments, the behavior confidence factor is a number between 0 and 1. In some embodiments, one way to calculate this confidence factor is to measure the amount of activity (such as number of steps) of the person 30 minutes prior to the measurements. The higher amount of activity in this period results in a lower value for the confidence factor. For example, the number of steps of the person 30 minutes prior to the measurement may be and number N. Then, $C_{beh}$ may be calculated as shown in Eq. (2)

$$\frac{TH - \min(N, TH)}{TH} \quad (2)$$

in which TH is an extreme threshold number (such as 10, 20, 50, 100, etc.) and min is the minimum function such that min (N,TH) returns the smaller value between N and TH.

Figure 16:
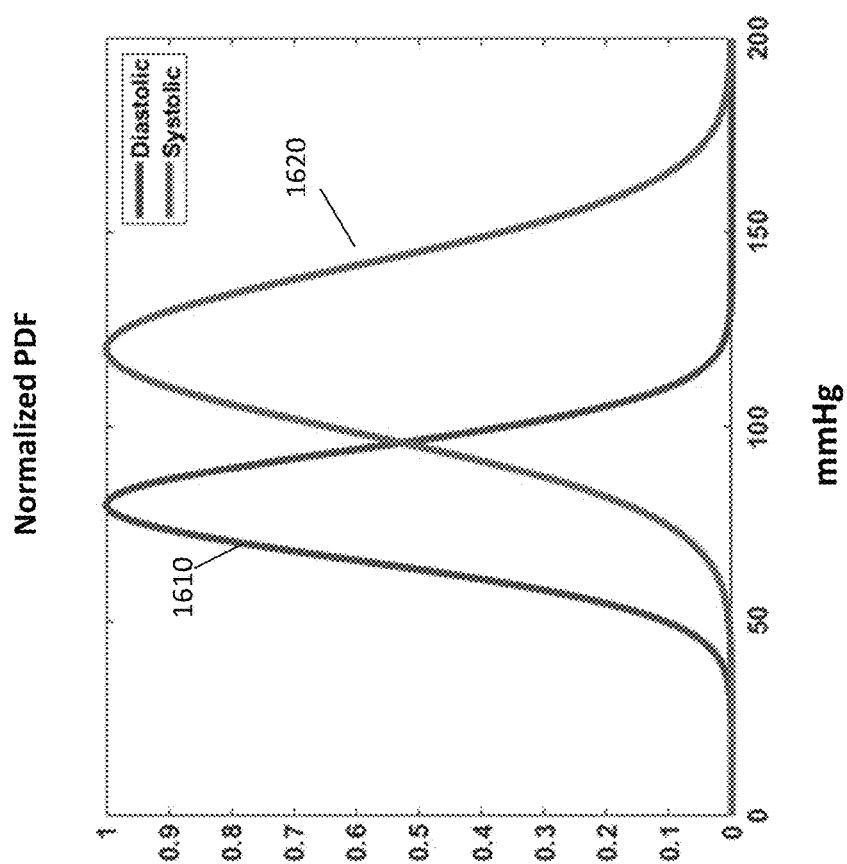
FIG. 16 illustrates a distribution graph set 1600 according to some embodiments.

Some embodiments determine alignment factor 1430 by comparing health measurements from one subject with the measurements and studies made in the general population. For example, some embodiments may use probability density functions (PDF) for the systolic, diastolic, and pulse pressure (difference between systolic and diastolic values) for general population determined by previous studies. One example of such distribution is shown in FIG. 16, which illustrates a distribution graph set 1600 according to some embodiments. Graph set 1600 includes a graph 1610 and a graph 1620 respectively showing PDF for the systolic and diastolic pressures for the general public according to some studies. Using this PDF, the likelihood of each measurement value may be calculated, that is, a confidence factor may be assigned to that measurement based on the likelihood of that measurement value in the PDF, as further described below.

In some embodiments, the health measurements for a subject is used to measure a physiological confidence factor $C_{phy}$. In some embodiments, the physiological confidence factor is a number between 0 and 1, and reflects the likelihood that the measurement is correct based on relevant PDF's for the general public and the subject's own historical data. The confidence factor $C_{phy}$ may be calculated as the value of the normalized PDF function at the measurement value. For each user the PDF is initialized with the general population PDF. Over time as the user makes more measurements, the PDF may be updated according to the new measurements, which makes the PDF personalized for that user.

Some embodiments determine a total confidence factor for the measurement as an overall assessment of the probability that the measurement is accurate. In some embodiments, the total confidence factor is calculated as the average of one or more specific confidence factors, such as the three described above. For example, the total confidence factor maybe the arithmetic average of the raw confidence factor, the behavior confidence factor, and the physiological confidence factor, described above, as shown in Eq. (3).

$$C_{meas} = (C_{raw} + C_{beh} + C_{phy})/3 \quad (3)$$

In some embodiments, if the total confidence factor for a measurement is lower than a threshold (for example, 0.6, 0.7, 0.8, or 0.9, etc.), the data assessment mechanism may send a coaching message to the subject or to the subjects caregiver to take new measurements by following guidelines for making accurate measurements.

In some embodiments, each health measurement for a subject may be stored along with the total confidence factor for that measurement. Further, when a group of measurements are considered together, the confidence factor for each of them may be used as a weight for that measurement. For example to determine an average of multiple measurements made in an extended period of time, the average measurement may be the weighted average of those multiple measurements.

Figure 17:
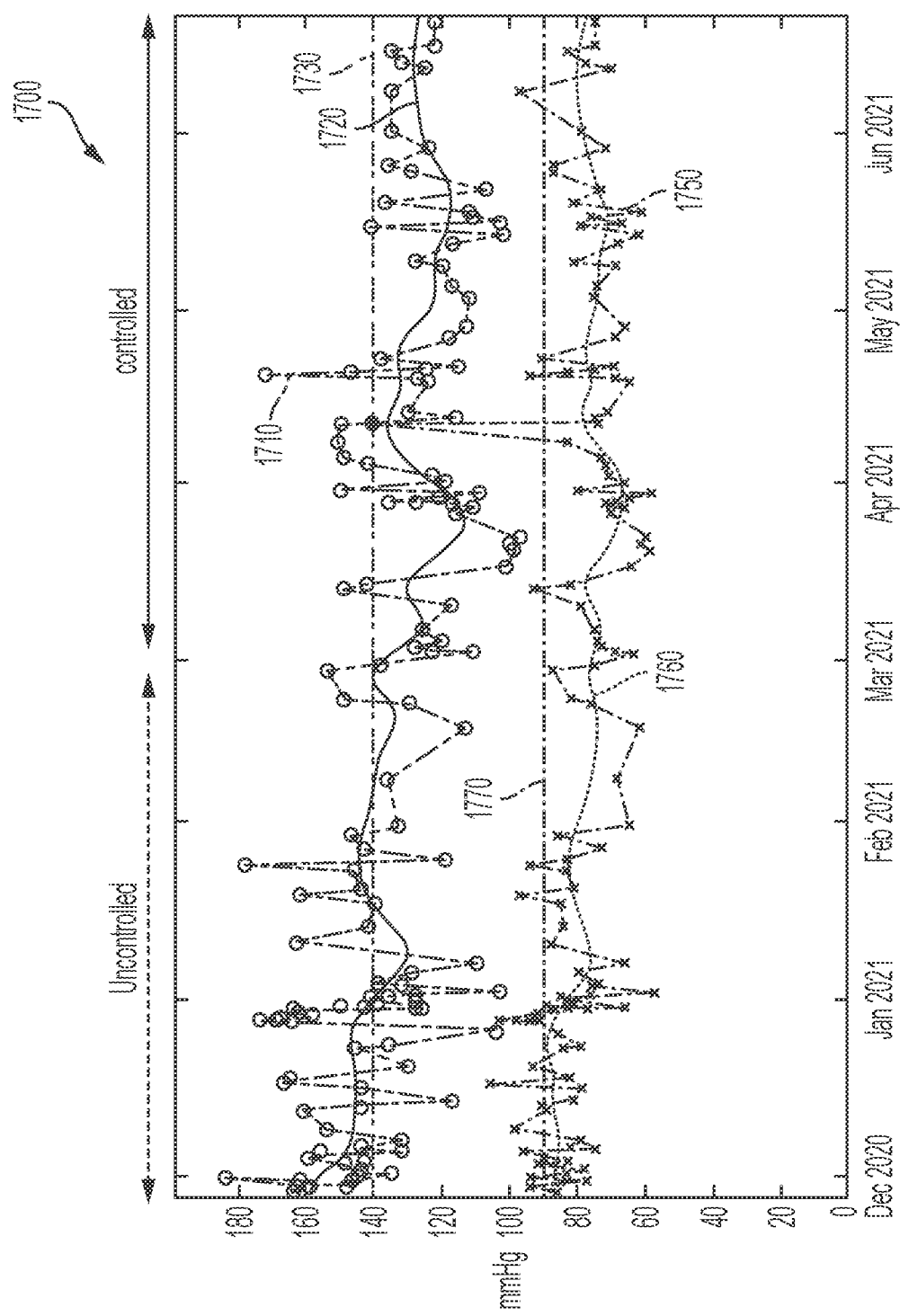
FIG. 17 depicts another example of utilizing the total confidence factor according to some embodiments.

FIG. 17 depicts another example of utilizing the total confidence factor according to some embodiments. In various embodiments, the mechanism illustrated in FIG. 17 may be utilized by a health monitoring system, or one or more modules in a health monitoring system.

In particular, FIG. 17 shows a diagram 1700 that displays data corresponding to systolic and diastolic pressures of a subject collected in a time period that includes December 2020 to June 2021. More specifically, diagram 1700 includes detailed data 1710 (hollow circles), trend graph (the top solid line graph), and health threshold line 1730 (the top solid horizontal line at 140 mmHg) for the systolic pressure. Moreover, diagram 1700 includes detailed data 1750 (crosses), trend graph 1760 (the bottom dashed line graph), and health threshold line 1770 (the bottom dashed horizontal line at around 90 mmHg) for the diastolic pressure. In various embodiments, these data may be derived and interpreted as follows.

The detailed data 1710 and 1750 may correspond to measurements (such as measuring the blood pressure or oxygen level) each made in consecutive short periods of time (such as one day, two day, three day, five day, or one week periods, etc.) during the extended period of time.

Further, to derive the trend of health factor, such as these blood pressures, the trend graphs 1720 and 1760 may be determined by the following process. First, a moving average of the corresponding detailed data is calculated, where the moving average spans a number of consecutive detailed data (such as 2, 3, 5, etc.). Moreover, the average may be a weighted average in which each point in the detailed data is weighted by the confidence factor for the corresponding measurement of that point. Further, the derived averages are fitted into a smooth function such as a cubic spline or a piece-wise polynomial curve, to derive the trend graph 1720 or 1760. The trend graphs, therefore, may show a smooth trend of the blood pressure change throughout the extended period of time.

Next, the trend graphs may be compared to some threshold criteria to derive a qualitative state for the health of the subject. For example, in diagram 1700, trend graph 1720 may be compared with the health threshold line 1730 and trend graph 1760 may be compared to health threshold line 1770. Based on these comparisons, in the example of diagram 1700 one may observe that during the period of time between December 2022 and March 2021, the trend of the systolic pressure, indicated by trend graph 1720 was generally near or above a maximum healthy value for the systolic pressure, as indicated by health threshold line 1730; while after March 2021, the trend of the systolic pressure was generally below that health threshold value. Therefore, one may decide that the blood pressure of the subject was in an uncontrolled state before March 2021, but change into a controlled state after that time, as indicated in diagram 1700.

Some embodiments may utilize multiple measurement devices to track a health factor. For example, for tracking the blood pressure of a subject, some embodiments may use multiple sensors such as the blood pressure cuff and a photoplethysmography (PPG) sensor that may be installed in a smartwatch or other mobile wearable devices.

Figure 18A:
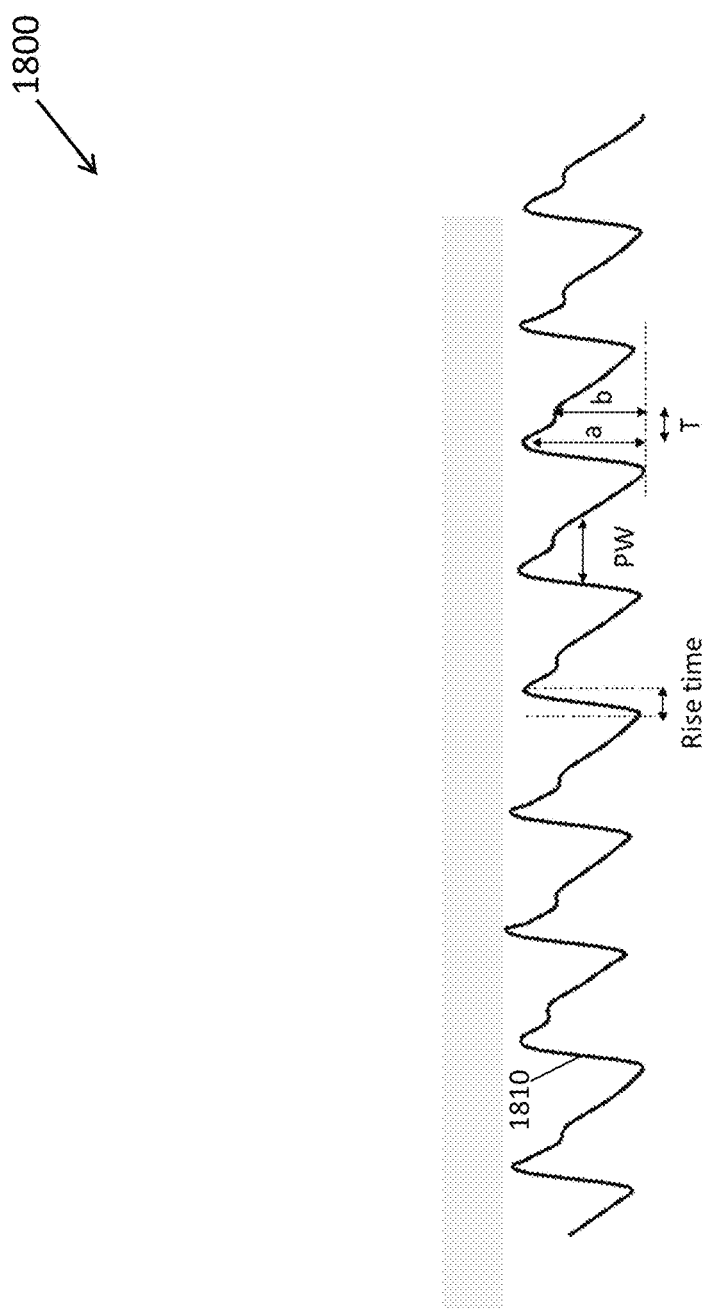
FIG. 18A shows a pulse signal 1800, illustrating different features of the waveform for the pulse signal according to some embodiments.

Moreover, in some embodiments, the health monitoring system, or one or more of its modules, may utilize different features in the waveform of the PPG for tracking changes in the health factor. FIG. 18A shows a pulse signal 1800, illustrating different features of the waveform for the pulse signal according to some embodiments. Pulse signal 1800 may be detected by a photoplethysmography (PPG) sensor or some similar sensors. For example, as shown in FIG. 18A, in the pulse waveform, the following features may be considered
  Statistical properties of the pulse rate at rest such as the mean and standard deviation of the resting heart rate excluding the sleep time in the past 24 hours.
  statistical properties of the pulse rate such as mean and standard deviation during sleep
  statistical properties of the pulse rate such as mean and standard deviation during activity
  Pulse width at different pulse heights (PW as shown in FIG. 18A)
  Pulse rise time (as shown in FIG. 18A)
  Ratio of the diastolic peak to the systolic peak (b/a where b and a the height of the diastolic and systolic peaks as shown in FIG. 18A)
  Distance (or time difference) between the systolic and the diastolic peaks (T as shown in FIG. 18A)
  The distance between the R wave of the ECG wave to the peak or valley of the subsequent PPG pulse. This is also called pulse transit time (PTT)

The above listed features may be used as parameters for training and machine learning module. More specifically, some embodiments utilize a machine learning technology to derive estimate blood pressure from the pulse waveform features. For example, the machine learning technology may be trained using the one or more of the above features derived from the PPG waveform of the subject at any time along with the measured blood pressure of the subject at that time. Over time, the machine learning algorithm may learn to estimate the blood pressure from the pulse waveform features. Further, upon detecting significant changes in the estimated blood pressure, the system may trigger a recommendation to the user to make a blood pressure measurement.

Figure 18B:
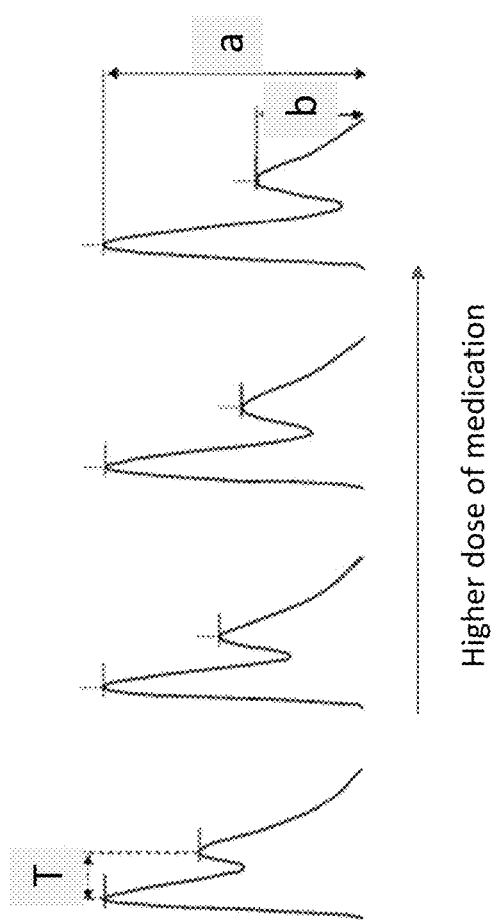
FIG. 18B shows an illustration 1850 for an exemplary change in morphology of waveform for PPG pulses of a patient resulting from taking higher doses of medication for lowering blood pressure according to an embodiment.

Moreover, in some embodiments, some changes in the features of the waveform may indicate changes in the health situation or behavior of a subject and trigger a coaching message. For example, some changes may indicate that a subject with hypertension is not taking her medications, triggering a recommendation or a reminder for taking the medication regularly. FIG. 18B shows an illustration 1850 for an exemplary change in morphology of waveform for PPG pulses of a patient resulting from taking higher doses of medication for lowering blood pressure according to an embodiment. More specifically, illustration 1850 includes four representative waveforms for PPG pulses of a patient at four consecutive time periods during which the patient has increased the dosage of a hypertension medication. Illustration 1850 shows that some features of the PPG waveform such as the height and distance between the systolic and diastolic peaks are changing with different dosage of hypertension medication. For instance, in the example of illustration 1850, upon increase in the dose of the medication, the ratio of the diastolic peak to the systolic peak (b/a listed above) has decreased while the distance T between the two peaks has increased over time.

Figure 19:
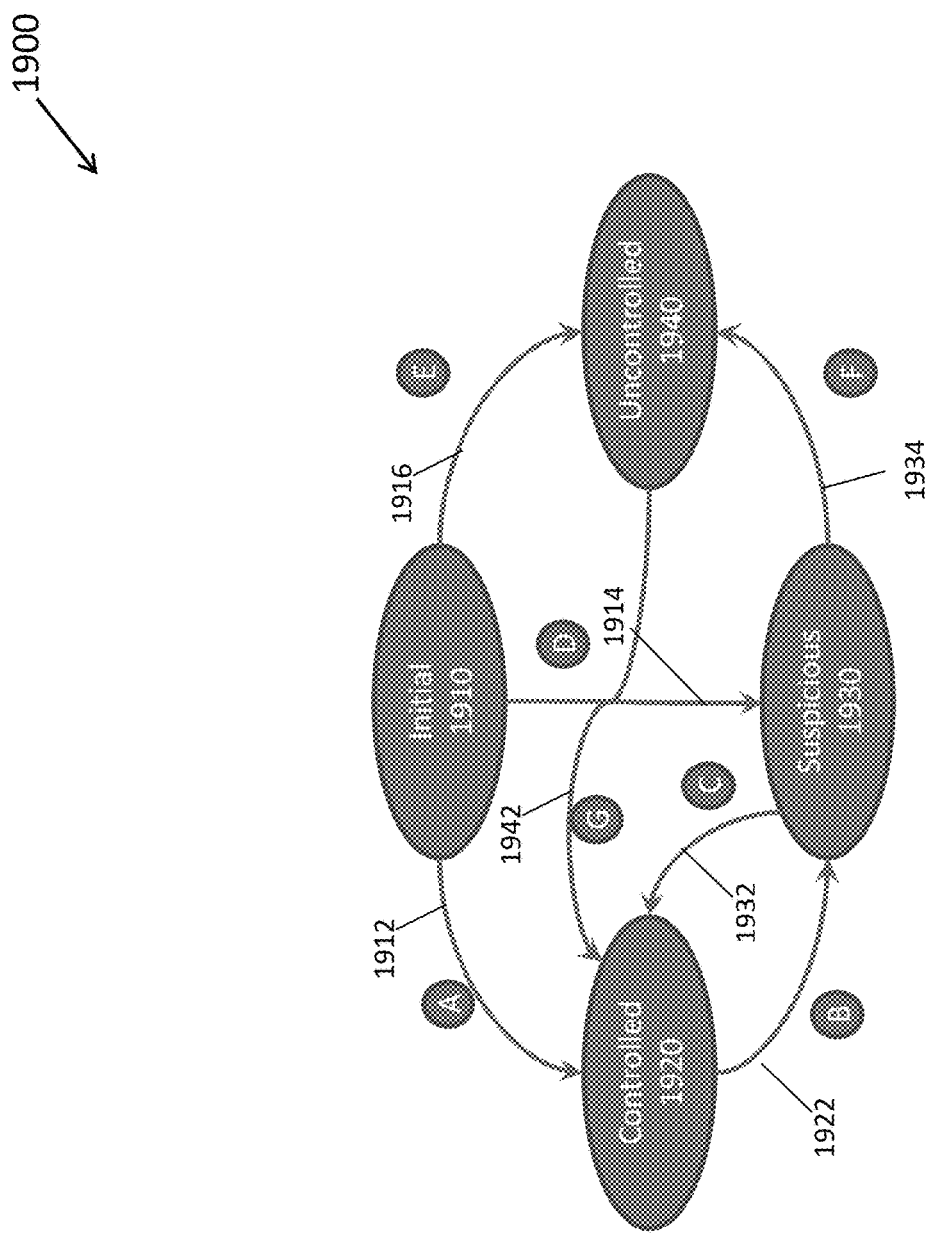
FIG. 19 shows a state diagram 1900 utilized to manage the hypertension according to some embodiments.

In some embodiments, the health monitoring system or its modules may use a state diagram for managing a health issue of a subject. FIG. 19 shows a state diagram 1900 utilized to manage the hypertension according to some embodiments. More specifically, state diagram 1900 includes four health states, initial state 1910, control the state 1920, suspicious state 1930, and uncontrolled state 1940. Moreover, state diagram 1900 includes transitions 1912, 1914, 1916, 1922, 1932, 1934, and 1942 with criteria further described below.

The transition criteria in state diagram 1900 may be determined based on values of three parameters, $N_x$, $BP\_OR_x$, and $BP\_EM_x$. $N_x$ is defined as the number of times that the blood pressure has been measured in the past x number of days. $BP\_OR_x$ is defined as the number of times that the blood pressure measurement has been out of a normal range in the past x days. And $BP\_EM_x$ is defined as the number of emergency blood pressure measurements in the past x days. As an example and for illustration, the blood pressure may be considered in the normal range if the systolic blood pressure is below 140 mmHg and the diastolic blood pressure is below 90 mmHg. Moreover, a blood pressure may be considered to be at the emergency level if the systolic blood pressure is above 180 mmHg or the diastolic blood pressure is above 120 mmHg. Moreover, for each of the states 1910, 1920, 1930, and 1940, a minimum number of blood pressure measurements may be recommended. For example, the recommended minimum number of blood pressure measurements for controlled state 1920 may be twice per week and for the other three states may be once every day.

Regarding the transitions, the state of a patient may undergo transition 1912 from initial state 1910 to control state 1920 when transition criterion (1912) below is satisfied:

$$N_{10} \geq 4 \ \& \ BP\_OR_{10}=0 \quad (1912),$$

that is, if the blood pressure has been measured at least four times in the past 10 days and it has not been out of range in any of those measurements.

Further, the state of the patient may undergo transition 1914 from initial state 1910 to suspicious state 1930 when transition criterion (1914) below is satisfied:

$$(N_{10} 4 \& BP\_OR_{10}=1 \& BP\_EM_{10}=0) \quad (1914),$$

that is, if the blood pressure has been measured at least four times in the past 10 days and it has been out of range once and it has never been at the emergency level.

On the other hand, the state of the patient may undergo transition 1916 from initial state 1910 to uncontrolled state 1940 when transition criterion (1916) below is satisfied:

$$(N_{10} 4 \& BP\_OR_{10} \geq 2) OR (BP\_EM_{10} \geq 1) \quad (1916),$$

that is, if the blood pressure has been measured at least four times in the past 10 days and it has been out of range at least twice, or if the blood pressure has been at the emergency level at least once in the past 10 days.

If the patient is in controlled state 1920, his state may undergo transition 1922 into suspicious state 1930 when transition criterion 1922 below is satisfied:

$$(BP\_OR_7 \geq 2) OR (BP\_EM_7 \geq 1) \quad (1922),$$

that is, if in the past seven days the blood pressure measurement has been out of range at least twice or has been at the emergency level at least once.

Once a patient is at suspicious state 1930, the patient's state may undergo transition 1932 back to the controlled state when transition criterion (1932) below is satisfied:

$$N_3 \geq 3 \& BP\_OR_3=0 \quad (1932),$$

that is, if the blood pressure has been measured at least three times in the past three days and it has never been out of range in the past three days.

The patient's state may, on the other hand, undergo transition 1934 from suspicious state 1930 to uncontrol the state in 1940 when transition criterion (1934) is satisfied:

$$(N_3 \geq 3 \& BP\_OR_3 \geq 2) OR$$

$$(BP\_EM_3 \geq 1) OR (N_7 \geq 4 \& BP\_OR_7 \geq 2) \quad (1934),$$

that is, if one of the following conditions is satisfied: 1) the blood pressure has been measured three times in the past three days and it has been out of range at least twice, 2) the blood pressure has been in the emergency level at least once, or 3) the blood pressure has been measured more than four times in the past seven days and it has been out of range at least twice.

Once the patient is in uncontrolled state 1940, the patient's state may undergo transition 1942 to controlled state 1920 when transition condition (1942) is satisfied:

$$N_3 \geq 3 \& BP\_OR_3=0 \quad (1942),$$

that is, if the blood pressure has been measured at least three times in the past three days and it has never been out of range.

In some embodiments, when the hypertension status is confirmed to be in uncontrolled state for a certain time interval (such as five days, one week, two weeks, etc.) an alert is generated for the care team for a proper intervention. This intervention might include increasing of the dosage of medication, consulting a physician, hospitalizing the patient, etc.

In some embodiments, the confidence factors are taken into account for the measurements used in the transition criteria above. For example, for a blood pressure measurement to be considered in a transition criterion, its confidence factor may be required to be above a minimum confidence factor (such as 0.7, 0.8, 0.9, etc.). Moreover, to determine the state of a patient, the system may utilize the trend mechanism described above in relation to FIG. 17. More specifically, the state of a patient may be considered to be in controlled or uncontrolled state based on the trend graphs for the health measurements in comparison with some criteria for those health measurements to be considered in a normal range or out of range.

The method explained above may be applied for automatic management of different chronic diseases such as hypertension, diabetes, heart failure, atrial fibrillation, etc. For example, in the case of heart failure, one or more types of health data such as physical activity, blood pressure, pulse oximeter, ECG, or weight of the patient may be collected on a continuous basis. The system may measure the reliability of the collected data using techniques similar to those explained above, and confidence factors may be calculated for the data. A personalized model may be created for the patient according to the health and behavioral data. The state of the disease including the stage of the disease may be determined and updated based on the health data. Health coaching may be provided for the patient according to the personalized model and the changes in the heart failure state may trigger the intervention alert for the care team, in the manners discussed above.

Each of the systems described above may comprise multiple modules. The modules may be implemented individually or their functions may be combined with the functions of other modules. Further, each of the modules may be implemented on individual components, or the modules may be implemented as a combination of components. For example, each of the modules may be implemented by a field-programmable gate array (FPGA), an application-specific integrated circuit (ASIC), a complex programmable logic device (CPLD), a printed circuit board (PCB), a combination of program able logic components and programmable interconnects, single CPU chip, a CPU chip combined on a motherboard, a general purpose computer, or any other combination of devices or modules capable of performing the tasks of the corresponding module. In some embodiments, one or more of the disclosed methods are stored in the form of programs on one or more non-transitory computer readable mediums. A computer readable medium can be a data storage module. A data storage module may comprise a random access memory (RAM), a read only memory (ROM), a programmable read-only memory (PROM), a field programmable read-only memory (FPROM), or other dynamic storage device for storing information and instructions to be used by another module, such as a data processing module or a search module. A data storage module may also include a database, one or more computer files in a directory structure, or any other appropriate data storage mechanism such as a memory.

In various embodiments, one or more of disclosed modules may be implemented via one or more computer programs for performing the functionality of the corresponding modules, or via computer processors executing those programs. In some embodiments, one or more of the disclosed modules may be implemented via one or more hardware units executing firmware for performing the functionality of the corresponding modules. In various embodiments, one or more of the disclosed modules may include storage media for storing data used by the module, or software or firmware programs executed by the module. In various embodiments, one or more of the disclosed modules or disclosed storage media may be internal or external to the disclosed systems. In some embodiments, one or more of the disclosed modules or storage media may be implemented via a computing "cloud", to which the disclosed system connects via a network connection and accordingly uses the external module or storage medium. In some embodiments, the disclosed storage media for storing information may include non-transitory computer-readable media, such as a CD-ROM, a computer storage, e.g., a hard disk, or a flash memory. Further, in various embodiments, one or more of the storage media may be non-transitory computer-readable media that store data or computer programs executed by various modules, or implement various techniques or flow charts disclosed herein.

Figure 20:
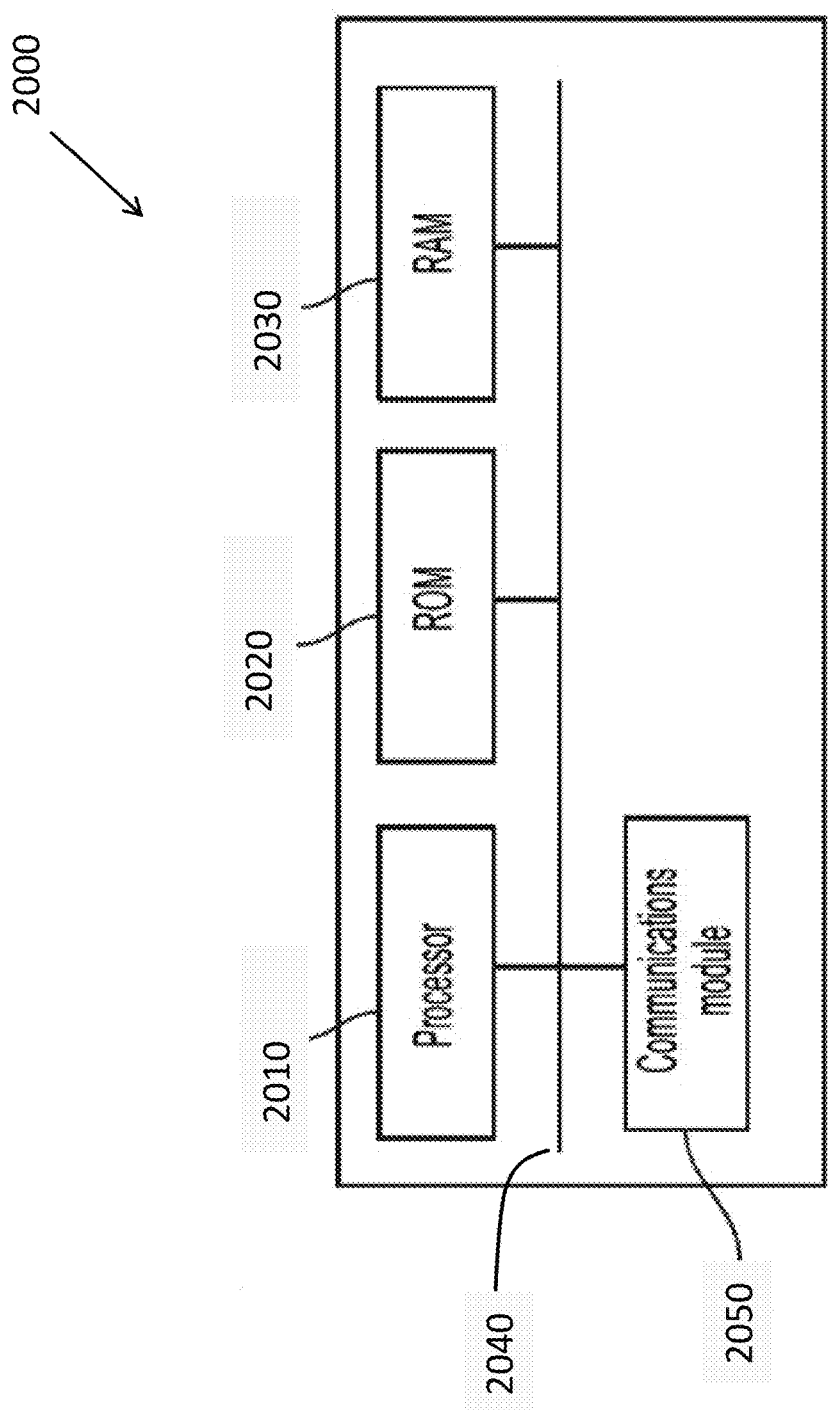
FIG. 20 schematically depicts an example of an implementation of a module 2000 according to some embodiments.

By way of example, FIG. 20 schematically depicts an example of an implementation of a module 2000 according to some embodiments. Module 2000 includes a processor 2010 (e.g., a microprocessor), at least one permanent memory module (e.g., ROM 2020), at least one transient memory module (e.g., RAM) 2030, a bus 2040, and a communication module 2050.

Processor 2010, ROM 2020, and RAM 2030 may be utilized to store and execute instructions performing the function of module 2000. Moreover, bus 2040 may allow communication between the processor and various other components of the controller. Communication module 2050 may be configured to allow sending and receiving signals.

The above detailed description refers to the accompanying drawings. The same or similar reference numbers may have been used in the drawings or in the description to refer to the same or similar parts. Also, similarly named elements may perform similar functions and may be similarly designed, unless specified otherwise. Details are set forth to provide an understanding of the exemplary embodiments. Embodiments, e.g., alternative embodiments, may be practiced without some of these details. In other instances, well known techniques, procedures, and components have not been described in detail to avoid obscuring the described embodiments.

The foregoing description of the embodiments has been presented for purposes of illustration only. It is not exhaustive and does not limit the embodiments to the precise form disclosed. While several exemplary embodiments and features are described, modifications, adaptations, and other implementations may be possible, without departing from the spirit and scope of the embodiments. Accordingly, unless explicitly stated otherwise, the descriptions relate to one or more embodiments and should not be construed to limit the embodiments as a whole. This is true regardless of whether or not the disclosure states that a feature is related to "a," "the," "one," "one or more," "some," or "various" embodiments. As used herein, the singular forms "a," "an," and "the" may include the plural forms unless the context clearly dictates otherwise. Further, the term "coupled" does not exclude the presence of intermediate elements between the coupled items. Also, stating that a feature may exist indicates that the feature may exist in one or more embodiments.

In this disclosure, the terms "include," "comprise," "contain," and "have," when used after a set or a system, mean an open inclusion and do not exclude addition of other, non-enumerated, members to the set or to the system.

Further, unless stated otherwise or deducted otherwise from the context, the conjunction "or," if used, is not exclusive, but is instead inclusive to mean and/or. Moreover, if these terms are used, a subset of a set may include one or more than one, including all, members of the set.

Further, if used in this disclosure, and unless stated or deducted otherwise, a first variable is an increasing function of a second variable if the first variable does not decrease and instead generally increases when the second variable increases. On the other hand, a first variable is a decreasing function of a second variable if the first variable does not increase and instead generally decreases when the second variable increases. In some embodiment, a first variable may be an increasing or a decreasing function of a second variable if, respectively, the first variable is directly or inversely proportional to the second variable.

The disclosed systems, methods, and apparatus are not limited to any specific aspect or feature or combinations thereof, nor do the disclosed systems, methods, and apparatus require that any one or more specific advantages be present, or problems be solved. Any theories of operation are to facilitate explanation, but the disclosed systems, methods, and apparatus are not limited to such theories of operation.

Modifications and variations are possible in light of the above teachings or may be acquired from practicing the embodiments. For example, the described steps need not be performed in the same sequence discussed or with the same degree of separation. Likewise various steps may be omitted, repeated, combined, or performed in parallel, as necessary, to achieve the same or similar objectives. Similarly, the systems described need not necessarily include all parts described in the embodiments, and may also include other parts not described in the embodiments. Accordingly, the embodiments are not limited to the above-described details, but instead are defined by the appended claims in light of their full scope of equivalents. Further, the present disclosure is directed toward all novel and non-obvious features and aspects of the various disclosed embodiments, alone and in various combinations and sub-combinations with one another.

While the present disclosure has been particularly described in conjunction with specific embodiments, many alternatives, modifications, and variations will be apparent in light of the foregoing description. It is therefore contemplated that the appended claims will embrace any such alternatives, modifications, and variations as falling within the true spirit and scope of the present disclosure.

What is claimed is:

1. A health monitoring system comprising:
a plurality of sensors configured to measure at least one parameter relating to a condition of a subject, wherein:
the plurality of sensors includes a blood pressure measurement device and a movement sensor;
the blood pressure measurement device is configured to generate health data including blood pressure raw data; and
the movement sensor is configured to generate behavioral data including data corresponding to body movements of the subject; and
a health monitoring module in communication with the plurality of sensors and including an automated data collection module that is configured to control automated measurements by at least a first sensor of the plurality of sensors, wherein:
the health monitoring module is configured to:

receive from the plurality of sensors measurement data including the health data and the behavioral data;
determine a reliability of the measurement data based on a total confidence factor and at least one of a variance of the health data and a variance of the behavioral data; and
based on the measurement data and the reliability of the measurement data,
determine a state of a disease of the subject;
and wherein:
the total confidence factor is determined based on at least one of a raw data confidence factor, a behavior confidence factor, and a physiological confidence factor;
the raw data confidence factor is determined based on a regularity of the blood pressure raw data;
the behavior confidence factor is determined based on the body movements within a time period before the measurement; and
the physiological confidence factor is determined based on a probability density function for a general population and corresponding to the measurements;
the automated data collection module is configured to trigger an action by the first sensor based on the reliability of the measurement data and the state of the disease; and
the action includes triggering a new automatic measurement by the first sensor or changing a frequency of automatic measurements by the first sensor.

2. The health monitoring system of claim 1, wherein the health monitoring module is further configured to:
receive from the plurality of sensors a plurality of measurements of the plurality of parameters;
derive a trend for the plurality of measurements; and
based on the trend, determine a health state for the subject.

3. The health monitoring system of claim 1, wherein the health monitoring module is further configured to:
store a plurality of measurements along with a plurality of total confidence factors corresponding to the plurality of measurements; and
derive an average of the plurality of measurements, wherein the average is a weighted average in which each measurement of the plurality of measurements is weighted by the corresponding total confidence factor.

4. The health monitoring system of claim 1, wherein:
the plurality of sensors includes a photoplethysmography (PPG) sensor; and
the health monitoring system further comprises a machine learning module configured to:
receive training data including training blood pressure data generated by the blood pressure measurement device and training PPG data generated by the PPG sensor;
derive from the training PPG data one or more training PPG features;
learn from the training data to determine the training blood pressure from the training PPG features;
receive real-time PPG data generated by the PPG sensor;
derive from the real-time PPG data one or more real-time PPG features; and
based on the real-time PPG features, determine a real-time blood pressure of the subject.

5. The health monitoring system of claim 1, wherein the health monitoring module is further configured to:
detect a critical event based on the measurement data;
include in a message a critical condition alert message; and
send the message to a health actor.

6. The health monitoring system of claim 1, wherein the plurality of sensors includes a wearable measurement device.

7. The health monitoring system of claim 1, wherein:
the health monitoring module further determines a health state of the subject based on a state diagram;:
the state diagram comprises a plurality of states that include an initial state, a controlled state, a suspicious state, and an uncontrolled state;
the health state of the subject is initialized as the initial state;
the health state of the subject transitions from a first state of the plurality of states to a second state of the plurality of states based on one or more values of one or more transition parameters; and
the one or more transition parameters correspond to a number of times that a blood pressure has been measured during a period of time, a number of times that the blood pressure has been out of a normal range during the period of time, or a number of emergency blood pressure measurements during the period of time.

8. A health monitoring system comprising:
a plurality of sensors configured to generate data corresponding to a subject, wherein:
the plurality of sensors includes a blood pressure measurement device, a movement sensor, and a photoplethysmography (PPG) sensor;
the blood pressure measurement device is configured to generate health data including blood pressure raw data;
the PPG sensor is configured to generate PPG data; and
the movement sensor is configured to generate behavioral data including body movement data;
a machine learning module configured to:
receive training data including the blood pressure raw data and the PPG data;
derive from the PPG data one or more PPG features;
learn from the training data to determine a blood pressure from the PPG features;
receive real-time PPG data generated by the PPG sensor;
derive from the real-time PPG data one or more real-time PPG features; and
based on the real-time PPG features, determine a real-time blood pressure; and
a health monitoring module in communication with the plurality of sensors and configured to:
receive from the plurality of sensors measurement data including the health data and the behavioral data;
receive from the machine learning module the real-time blood pressure;
based on the measurement data and the real-time blood pressure, determine a state of a disease; and
based on at least one of the state of the disease and a total confidence factor, trigger an action by at least one of the plurality of sensors, wherein the action includes an automatic measurement by the at least one of the plurality of sensors,
wherein:
the total confidence factor is determined based on at least one of a raw data confidence factor, a behavior confidence factor, and a physiological confidence factor;

the raw data confidence factor is determined based on a regularity of the blood pressure raw data;

the behavior confidence factor is determined based on the body movements within a time period before the measurement; and the physiological confidence factor is determined based on a probability density function for a general population and corresponding to the measurements.

9. The health monitoring system of claim 8, wherein the health monitoring module is further configured to:

determine a reliability of the measurement data based on a variance of the blood pressure raw data and body movement data; and further include in the determining the state of the disease the reliability of the measurement data.

10. The health monitoring system of claim 9, wherein the health monitoring module includes an automated data collection module configured to:

control automated measurements by at least a first sensor of the plurality of sensors; and trigger an action by the first sensor based on the reliability of the measurement data and the state of the disease, wherein:

the action includes triggering a new automatic measurement by the first sensor or changing a frequency of automatic measurements by the first sensor.

11. The health monitoring system of claim 10, wherein the health monitoring module is further configured to:

store a plurality of measurements along with a plurality of total confidence factors corresponding to the plurality of measurements; and derive an average of the plurality of measurements, wherein the average is a weighted average in which each measurement of the plurality of measurements is weighted by the corresponding total confidence factor.

12. The health monitoring system of claim 8, wherein the health monitoring module is further configured to:

receive from the plurality of sensors a plurality of measurements of a plurality of parameters;

derive a trend for the plurality of measurements; and based on the trend, determine a health state for the subject.

* * * * *